United States Patent
Marczyk et al.

(10) Patent No.: US 11,553,855 B2
(45) Date of Patent: Jan. 17, 2023

(54) DEVICES AND METHODS FACILITATING SLEEVE GASTRECTOMY AND OTHER PROCEDURES

(71) Applicant: Covidien LP, Mansfield, MA (US)

(72) Inventors: Stanislaw Marczyk, Stratford, CT (US); Stanislaw Kostrzewski, Newtown, CT (US); Andrew Miesse, Durham, CT (US); Sachin Shah, Milford, CT (US)

(73) Assignee: Covidien LP, Mansfield, MA (US)

( * ) Notice: Subject to any disclaimer, the term of this patent is extended or adjusted under 35 U.S.C. 154(b) by 732 days.

(21) Appl. No.: 16/223,586

(22) Filed: Dec. 18, 2018

(65) Prior Publication Data
US 2019/0117114 A1    Apr. 25, 2019

Related U.S. Application Data

(63) Continuation of application No. 14/491,660, filed on Sep. 19, 2014, now Pat. No. 10,159,425.
(Continued)

(51) Int. Cl.
*A61B 5/06* (2006.01)
*A61F 5/00* (2006.01)
(Continued)

(52) U.S. Cl.
CPC ............ *A61B 5/065* (2013.01); *A61F 5/0076* (2013.01); *A61F 5/0089* (2013.01); *A61B 1/313* (2013.01);
(Continued)

(58) Field of Classification Search
CPC .... A61B 2017/00278; A61B 2017/306; A61B 17/0487; A61B 2017/003; A61B 2017/00818
See application file for complete search history.

(56) References Cited

U.S. PATENT DOCUMENTS 2,067,031 A  1/1937  Wappler
3,227,154 A  1/1966  Cook
(Continued)

FOREIGN PATENT DOCUMENTS

CN    1809310 A    7/2006
CN    201365906 Y   12/2009
(Continued)

OTHER PUBLICATIONS

Canadian Office Action dated Mar. 31, 2021 corresponding to counterpart Patent Application CA 2,868,537.
(Continued)

*Primary Examiner* — Baisakhi Roy
(74) *Attorney, Agent, or Firm* — Carter, DeLuca & Farrell LLP

(57) ABSTRACT

A device for use in bariatric surgery includes a flexible hollow tube extending from a proximal end to a distal end and defines a channel therebetween. A series of openings is defined in a distal portion of the tube allowing for fixation of tissue using suction. A flexible member has an initial position disposed alongside the tube and is deployable to a subsequent position in which the flexible member engages a greater curvature of a stomach. The flexible member is configured to be deployable to automatically assume a shape of a greater curvature of a stomach. The flexible member includes a bulging region and a tapering region when deployed. The flexible member is releasably attached to the distal end of the tube.

10 Claims, 13 Drawing Sheets

Related U.S. Application Data

(60) Provisional application No. 61/901,870, filed on Nov. 8, 2013.

(51) Int. Cl.

| | | |
|---|---|---|
| A61B 17/06 | (2006.01) | |
| A61B 1/313 | (2006.01) | |
| A61B 17/04 | (2006.01) | |
| A61B 17/11 | (2006.01) | |
| A61B 17/00 | (2006.01) | |
| A61B 17/30 | (2006.01) | |
| A61B 90/30 | (2016.01) | |

(52) U.S. Cl.
CPC ..... *A61B 17/0487* (2013.01); *A61B 17/06109* (2013.01); *A61B 17/1114* (2013.01); *A61B 2017/00278* (2013.01); *A61B 2017/00818* (2013.01); *A61B 2017/306* (2013.01); *A61B 2090/309* (2016.02); *A61F 5/0036* (2013.01); *A61F 5/0083* (2013.01)

(56) References Cited

U.S. PATENT DOCUMENTS

| | | | |
|---|---|---|---|
| 3,739,784 A | 6/1973 | Itoh | |
| 4,328,805 A | 5/1982 | Akopov et al. | |
| 4,403,604 A | 9/1983 | Wilkinson et al. | |
| 4,625,594 A | 12/1986 | Janke | |
| 4,744,363 A | 5/1988 | Hasson | |
| 5,179,938 A | 1/1993 | Lonky | |
| 5,246,456 A | 9/1993 | Wilkinson | |
| 5,297,536 A | 3/1994 | Wilk | |
| 5,325,848 A | 7/1994 | Adams et al. | |
| 5,345,949 A | 9/1994 | Shlain | |
| 5,358,496 A | 10/1994 | Ortiz et al. | |
| 5,382,231 A | 1/1995 | Shlain | |
| 5,401,241 A | 3/1995 | Delany | |
| 5,458,131 A | 10/1995 | Wilk | |
| 5,465,709 A | 11/1995 | Dickie et al. | |
| 5,549,621 A | 8/1996 | Bessler | |
| 5,718,666 A | 2/1998 | Alarcon | |
| 6,663,639 B1 | 12/2003 | Laufer et al. | |
| 6,736,828 B1 | 5/2004 | Adams | |
| 7,153,131 B2 | 12/2006 | Crohn | |
| 7,666,195 B2 | 2/2010 | Kelleher | |
| 7,744,613 B2 | 6/2010 | Ewers et al. | |
| 7,918,869 B2 | 4/2011 | Saadat et al. | |
| 8,092,378 B2 * | 1/2012 | Roth | A61B 17/072 600/206 |
| 8,092,472 B2 * | 1/2012 | Cerier | A61B 5/065 606/139 |
| 8,147,502 B2 | 4/2012 | Albrecht et al. | |
| 8,192,448 B2 | 6/2012 | Bessler et al. | |
| 8,454,503 B2 | 6/2013 | Roth et al. | |
| 8,663,149 B2 | 3/2014 | Gagner et al. | |
| 10,159,425 B2 * | 12/2018 | Marczyk | A61B 5/065 |
| 2002/0091395 A1 | 7/2002 | Gabbay | |
| 2004/0006351 A1 | 1/2004 | Gannoe et al. | |
| 2004/0092974 A1 | 5/2004 | Gannoe et al. | |
| 2005/0119674 A1 | 6/2005 | Gingras | |
| 2005/0203489 A1 | 9/2005 | Saadat et al. | |
| 2005/0251158 A1 | 11/2005 | Saadat et al. | |
| 2006/0200004 A1 | 9/2006 | Wilk | |
| 2006/0241344 A1 | 10/2006 | Wilk | |
| 2006/0241570 A1 | 10/2006 | Wilk | |
| 2007/0032702 A1 | 2/2007 | Ortiz | |
| 2008/0051823 A1 * | 2/2008 | Makower | A61B 17/1285 606/192 |
| 2008/0249404 A1 | 10/2008 | Mikkaichi et al. | |
| 2009/0012512 A1 * | 1/2009 | Utley | A61B 18/1492 606/34 |
| 2009/0012542 A1 * | 1/2009 | N'diaye | A61F 5/0079 606/153 |
| 2009/0171382 A1 * | 7/2009 | Dillon | A61F 5/0089 606/192 |
| 2009/0276055 A1 | 11/2009 | Harris et al. | |
| 2010/0082046 A1 * | 4/2010 | Harris | A61F 5/0079 606/139 |
| 2010/0179417 A1 | 7/2010 | Russo | |
| 2011/0178454 A1 | 7/2011 | Gagner et al. | |
| 2011/0288576 A1 | 11/2011 | Hoffman | |
| 2012/0165608 A1 | 6/2012 | Banik et al. | |
| 2012/0184981 A1 | 7/2012 | Pecor et al. | |
| 2012/0239061 A1 | 9/2012 | Mathur | |
| 2013/0165774 A1 | 6/2013 | Nocca | |
| 2014/0012353 A1 * | 1/2014 | Prescott | A61N 5/0613 607/88 |
| 2014/0018722 A1 | 1/2014 | Scott et al. | |
| 2014/0073858 A1 * | 3/2014 | Sherwinter | A61B 90/30 600/249 |
| 2014/0088487 A1 * | 3/2014 | Harris | A61M 5/14276 604/20 |
| 2014/0114121 A1 * | 4/2014 | Trivedi | A61F 5/0089 600/37 |
| 2014/0243640 A1 * | 8/2014 | O'Dea | A61B 5/061 600/373 |
| 2015/0057519 A1 * | 2/2015 | Ben-David | A61B 5/6859 607/40 |
| 2017/0079823 A1 * | 3/2017 | Gagner | A61F 5/0083 |
| 2017/0266027 A1 * | 9/2017 | Sharma | A61F 5/0079 |

FOREIGN PATENT DOCUMENTS

| | | |
|---|---|---|
| CN | 102626536 A | 8/2012 |
| EP | 2246013 A1 | 11/2010 |
| ES | 2326937 A1 | 10/2009 |
| FR | 2708456 A1 | 2/1995 |
| JP | 2008161686 A | 7/2008 |
| JP | 3178309 U | 9/2012 |
| JP | 2013529487 A | 7/2013 |
| WO | 02096327 A2 | 12/2002 |
| WO | 03075979 A2 | 9/2003 |
| WO | 2009097585 A1 | 8/2009 |
| WO | 2012138737 A1 | 10/2012 |
| WO | 2012141679 A1 | 10/2012 |
| WO | 2013018079 A1 | 2/2013 |
| WO | 2013123235 A1 | 8/2013 |
| WO | 2014062881 A1 | 4/2014 |

OTHER PUBLICATIONS

Canadian Office Action dated Dec. 3, 2020, issued in corresponding CA Application No. 2,868,537, 6 pages.
European Search Report, dated Mar. 19, 2015, corresponding to European Application No. 14192226.0; 7 pages.
European Search Report, dated Mar. 24, 2015, corresponding to European Application No. 14192416.7; 7 pages.
International Search Report and Written Opinion of hte International Searching Authoirity, dated Jul. 12, 2016, corresponding to International Application No. PCT/US2016/028046; 12 total pages.
Dietel et al., "Endoscopy of Vertical Banded Gastroplasty," The American Surgeon, May 1989, vol. 55; pp. 287-890.
Dietel et al., "Vertical Banded Gastroplasty: Results in 233 Patients," The Canadian Journal of Surgery, Sep. 1986, vol. 29, No. 5; pp. 322-324.
Mason et al., "Vertical Gastroplasty: Evolution of Vertical Banded Gastroplasty,"World Journal of Surgery, Sep. 1998, vol. 22, No. 9; pp. 919-924.
Mervyn Deitel, "Vertical Banded Gastroplasty: Results in 233 Patients", The Canadian Journal of Surgery, Sep. 1986, 322-324, vol. 29., No. 5., Toronto Canada.
Mervyn Deitel, "Endoscopy of Vertical Banded Gastroplasty", The American Surgeon, May 1989, 287-290, vol. 55, Toronto Canada.
Edward E. Mason, "Vertical Gastroplasty: Evolution of Vertical Banded Gastroplasty", World Journal of Surgery, Sep. 1998, 919-924, vol. 22, No. 9, Iowa City, Iowa.
Shinya Tanimura, "Intracorporeal Billroth 1 Reconstruction by Triangulating Stapling Technique After . . . " Surg Laparosc Endosc Percutan Tech, Feb. 2008, 54-58, vol. 18, No. 1.

(56) References Cited

OTHER PUBLICATIONS

Antonio Lacy, "Revisional Surgery After Sleeve Gastrectomy", Surg Laparosc Endosc Percutan Tech, Oct. 2010, 351-356, vol. 20, No. 5., Lippincott Williams & Wilkins.
Extended European Search Report dated Sep. 17, 2015, corresponding to European Patent Application 15167339.9; 10 pages.
Extended European Search Report dated Oct. 1, 2015, corresponding to European Application No. 15167342.3; 7 pages.
European Search Report dated Dec. 2, 2015, corresponding to European Application No. 151772332; 7 pages.
European Search Report, dated Mar. 24, 2017, corresponding to European Application No. 16199748.1; 5 pages.
European Communication dated Feb. 1, 2017, corresponding to European Application No. 14192226.0; 5 pages.
Chinese Office Action (with English Summary Form), dated Jan. 29, 2018, corresponding to Chinese Application No. 2014106429044; 7 total pages.
Australian Examination Report No. 1, dated Jun. 20, 2018, corresponding to Australian Application No. 2014240327; 3 pages.
Japanese Office Action (with English translation), dated Jun. 22, 2018, corresponding to Japanese Application No. 2014-217122; 7 total pages.

\* cited by examiner

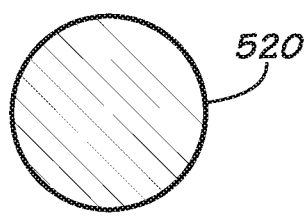
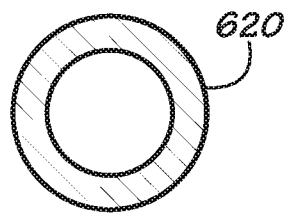
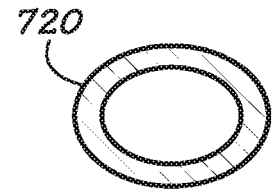
FIG. 16A  FIG. 16B  FIG. 16C
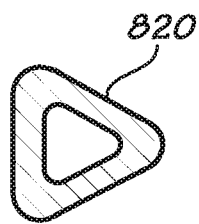
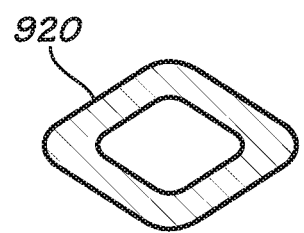
FIG. 16D  FIG. 16E
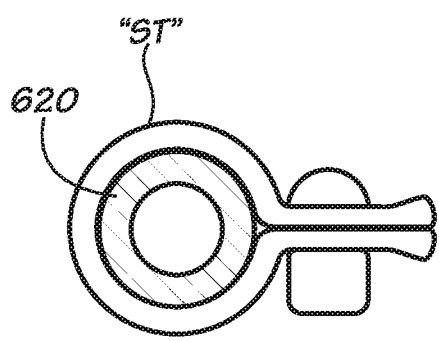
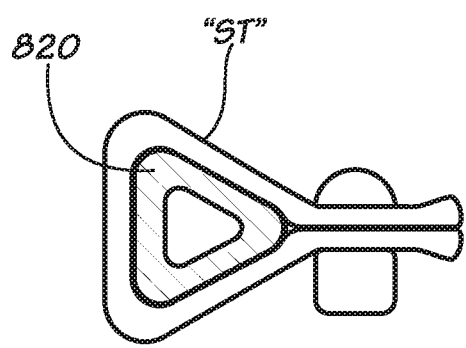
FIG. 17  FIG. 18

DEVICES AND METHODS FACILITATING SLEEVE GASTRECTOMY AND OTHER PROCEDURES

CROSS-REFERENCE TO RELATED APPLICATION

The present application is a continuation of U.S. patent application Ser. No. 14/491,660, filed Sep. 19, 2014, which claims the benefit of and priority to U.S. Provisional Application Ser. No. 61/901,870, filed Nov. 8, 2013, the entire contents of which is incorporated herein by reference.

BACKGROUND

Technical Field

The present disclosure relates generally to gastrointestinal surgery, such as, for example, sleeve gastrectomy, and to devices and methods that facilitate performing resection of gastric and other tissue.

Background of Related Art

Obesity is reaching epidemic proportions in many regions of the world, particularly in the United States. In order to treat obesity, various surgical procedures have been developed including, for example, gastric bypass, adjustable gastric banding, and sleeve gastrectomy. The goal in each of these procedures is to reduce the stomach capacity to restrict the amount of food that the patient can eat. The reduced stomach capacity, in turn, results in a feeling of fullness for the patient after ingesting a relatively smaller amount of food. Thus, the patient can achieve significant weight loss.

Sleeve gastrectomy involves transecting a stomach, e.g., using a stapling device or other suitable device, to reduce a stomach volume. Sleeve gastrectomy procedures are often aided by the use of a bougie, which serves as a guide or template for transecting the stomach to the appropriate configuration while inhibiting inadvertent transection of stomach or esophageal tissue. Once the stomach has been appropriately transected, the bougie is removed and a leak test is performed to determine whether there are any areas of extravasation.

There is a need for a device and/or method of positioning and stabilizing a stomach, or other hollow organ, to avoid shifting of the sides of the organ with respect to one another during transection, stapling, etc., in a surgical procedure. There is a need for a simpler, more convenient way to perform a leak test, visualize the transected tissue, etc.

SUMMARY

In an aspect of the present disclosure, a medical device comprises: a flexible hollow tube extending from a proximal end to a distal end and defining a channel therebetween, a series of openings being defined in a distal portion of the tube allowing for fixation of tissue using suction; a flexible member having an initial position disposed alongside the tube and being deployable to a subsequent position in which the flexible member engages a greater curvature of a stomach, the application of suction placing the tube along a lesser curvature of a stomach, fixing anterior and posterior walls of a stomach, and preventing their movement, the tube being visible under stomach tissue, the flexible member being configured to be deployable to automatically assume a shape of a greater curvature of a stomach, the flexible member including a bulging region and a tapering region when deployed, wherein the flexible member includes at least one illumination device.

The medical device can include a tube that has a proximal end that is open. The medical device preferably has a tube with a distal portion that is tapered. The medical device can further comprise a release wire for separating the flexible member from the tube.

A distal end of the flexible member can includes a balloon. The balloon is desirably shaped to position the flexible member in the stomach.

In certain embodiments, the flexible member includes a hinge adjacent a distal end of the flexible member. The flexible member can be selected from the group consisting of a rod and a tube. The flexible member is desirably made of a flexible resilient material.

The medical device, in certain embodiments, has a flexible member with a distal end attached to the distal end of the tube, and a proximal end manipulable from outside a patient's body.

In certain embodiments, the device includes a coupling device that holds the flexible member to the tube. The coupling device can slidably attach an intermediate portion of the flexible member to an intermediate portion of the tube.

The flexible member can be deployable to align a stomach by evening out anterior and posterior walls of a stomach and by pushing the tube and the openings in the tube towards a lesser curvature of a stomach.

In certain preferred embodiments, the proximal end of the tube is configured for connection to a suction source.

The tube has a cross-sectional shape that may be selected from the group consisting of triangular, diamond, elliptical, and tapered.

The tube may include at least one illumination device. At least one of the tube or the flexible member may include a vision device. The flexible member can have multiple attachments to the tube, the attachments being distributed down a length of the tube. The flexible member can include a distal end releasably attached to the distal end of the tube.

In certain preferred embodiments, the flexible member has a plurality of illumination devices distributed across its length.

In an aspect of the present disclosure, a medical device comprises a flexible hollow tube extending from a proximal end to a distal end and defining a channel therebetween. A series of openings is defined in a distal end portion of the tube allowing for fixation of tissue using suction. The medical device further includes a flexible member having an initial position disposed alongside the tube and deployable to a subsequent position in which the tube engages a greater curvature of a stomach. Application of suction places the tube along a lesser curvature of a stomach, fixing anterior and posterior walls of the stomach, and preventing their movement. The tube is visible under stomach tissue. The flexible member is configured to be deployable to automatically assume the shape of a greater curvature of the stomach. The flexible member includes a bulging region and a tapering region. The flexible member is releasably attached to the distal end of the tube.

In embodiments, the proximal end of the hollow tube may be open. The distal end of the tube may be tapered. The medical device can include a release wire for separating the flexible member from the tube. The medical device may further include a balloon at the distal end of the flexible member. The balloon may be shaped to position the flexible member in the stomach. The flexible member may include a hinge adjacent a distal end of the flexible member.

The flexible member may be a rod or tube of a flexible resilient material having a distal end attached to the distal end of the tube. The flexible member may include a proximal end manipulable from outside a patient's body. The tube may be made of silicone.

In aspects of the present disclosure, the medical device may include a coupling device that holds the flexible member to the tube. The coupling device can slidably attach an intermediate portion of the flexible member to an intermediate portion of the tube. The flexible member or movable element can be deployable to align the stomach by evening out the anterior and posterior walls of the stomach and by pushing the tube and a perforated area of the tube towards the lesser curvature of the stomach. Suction can be applied at the proximal end of the tube. Air or colored fluid can be instilled into a proximal end of the tube to perform a leak test.

The tube can have a cross-sectional shape selected from the group consisting of triangular, diamond, elliptical, and tapered. The tube, member, or both, can include at least one illumination device. The at least one illumination device can be an LED. The tube, member, or both, can include a vision device. The vision device can be a camera or a scope.

In another aspect of the present disclosure, a medical device comprises a flexible hollow tube extending from a proximal end to a distal end and defines a channel therebetween. A series of openings is defined in a distal end portion of the tube allowing for fixation of tissue using suction. The medical device further includes a flexible member having an initial position disposed alongside the tube and deployable to a subsequent position in which the flexible member engages a greater curvature of a stomach. The application of suction places the tube along a lesser curvature of the stomach, fixing anterior and posterior walls of the stomach, and preventing their movement. The tube is visible under stomach tissue. The flexible member is configured to be deployable to automatically assume the shape of the greater curvature. The flexible member includes a bulging region and a tapering region. The flexible member has multiple attachments to the tube distributed down a length of the tube. The flexible member includes a distal end releasably attached to the distal end of the tube.

In embodiments, the proximal end of the hollow tube can be open. The distal end of the tube can be tapered. The medical device may include a release wire for separating the member from the tube at the attachments. The medical device can further include a balloon at the distal end of the member. The balloon may be shaped in a manner so as to position the flexible member in the stomach.

The flexible member may be a rod or tube of a flexible resilient material having a distal end attached to the distal end of the tube, and a proximal end manipulable from outside a patient's body. The tube can be made of silicone.

The medical device may include a coupling device that holds an intermediate portion of the flexible member to the tube. The coupling device can slidably attach the intermediate portion of the member to an intermediate portion of the tube. The flexible member can be deployable to align the stomach by evening out the anterior and posterior walls of the stomach and by pushing the tube and a perforated area of the tube towards the lesser curvature of the stomach. Suction can be applied at the proximal end of the tube. Air or colored fluid can be instilled into a proximal end of the tube to perform a leak test.

The tube can have a cross-sectional shape selected from the group consisting of triangular, diamond, elliptical, and tapered. The tube, member, or both, can include at least one illumination device. The at least one illumination device can be an LED. The tube, member, or both, can include a vision device. The vision device can be a camera or a scope.

In a further aspect of the present disclosure, a medical device comprises a flexible hollow tube extending from a proximal end to a distal end and defines a channel extending therebetween. A series of openings is defined in a distal end portion of the tube allowing for fixation of tissue using suction. The medical device further includes a flexible member having an initial position disposed alongside the tube and deployable to a subsequent position in which the flexible member engages a greater curvature of a stomach. Application of suction places the tube along a lesser curvature of the stomach, fixing anterior and posterior walls of the stomach, and preventing their movement. The tube is visible under stomach tissue. The flexible member is configured to be deployable to automatically assume a shape of a greater curvature of the stomach. The flexible member includes a bulging region and a tapering region. The medical device further includes an expandable element disposed alongside the distal end of the tube.

In embodiments, the expandable element is an inflatable balloon. The balloon may be inflatable to enlarge an effective diameter of the medical device. In some embodiments, the expandable element may be a lever pivotably attached to the distal end of the tube. The lever may be pivotable in two directions.

The proximal end of the hollow tube may be open. The distal end of the tube may be tapered. The medical device may include a release wire for separating the member from the tube. The expandable element may be visible through stomach tissue. The expandable element may be used to indicate a location for an initial stapling and/or cutting operation.

The flexible member may be a rod or tube of a flexible resilient material having a distal end attached to the distal end of the tube, and a proximal end manipulable from outside a patient's body. The tube may be made of silicone.

In embodiments, the medical device may include a coupling device that holds the flexible member to the tube. The coupling device can slidably attach an intermediate portion of the member to an intermediate portion of the tube. The flexible member can be deployable to align the stomach by evening out the anterior and posterior walls of the stomach and by pushing the tube and a perforated area of the tube towards the lesser curvature of the stomach. Suction can be applied at the proximal end of the tube. Air or colored fluid can be instilled into a proximal end of the tube to perform a leak test.

The tube can have a cross-sectional shape selected from the group consisting of triangular, diamond, elliptical, and tapered. The tube, member, or both, can include at least one illumination device. The at least one illumination device can be an LED. The tube, member, or both, can include a vision device. The vision device can be a camera or a scope.

In another aspect of the present disclosure, a medical device comprises a flexible hollow tube extending from a proximal end to a distal end and defines a channel therebetween. At least one opening is defined in the distal end of the tube. The medical device further includes a flexible member having an initial position disposed alongside the tube and is deployable to a subsequent position. The flexible member is configured to be deployable to automatically assume a shape of a greater curvature of a stomach. The medical device further includes a reusable portion having a first tank of fluid, a second tank for receiving material, and a third tank communicating with atmospheric pressure. The reusable portion has a first valve, a second valve, and a third valve. The first valve and second valve each have a first position, a second position, and a third position. The channel is delivered with pressurized fluid when the first valve and the second valve are moved to the first position.

In embodiments, the second position of the first valve and the second valve is a closed position. The third valve may have a position in which a vacuum is provided to the channel. The device can further comprise a safety feature preventing the third valve from moving to an open position unless the first valve and the second valve are moved to the second position. The second position of the first valve and the second valve may be a closed position.

BRIEF DESCRIPTION OF THE DRAWINGS

Various aspects and features of the present disclosure are described herein with reference to the drawings, wherein:

FIGS. 16A through 16 E are cross-sectional views of tubes of a medical device according to embodiments of the present disclosure;

FIG. 17 is a cross-sectional view of a tube of a medical device according to embodiments of the present disclosure;

FIG. 18 is a cross-sectional view of a tube of a medical device according to embodiments of the present disclosure;

DETAILED DESCRIPTION OF EMBODIMENTS

Figure 1:
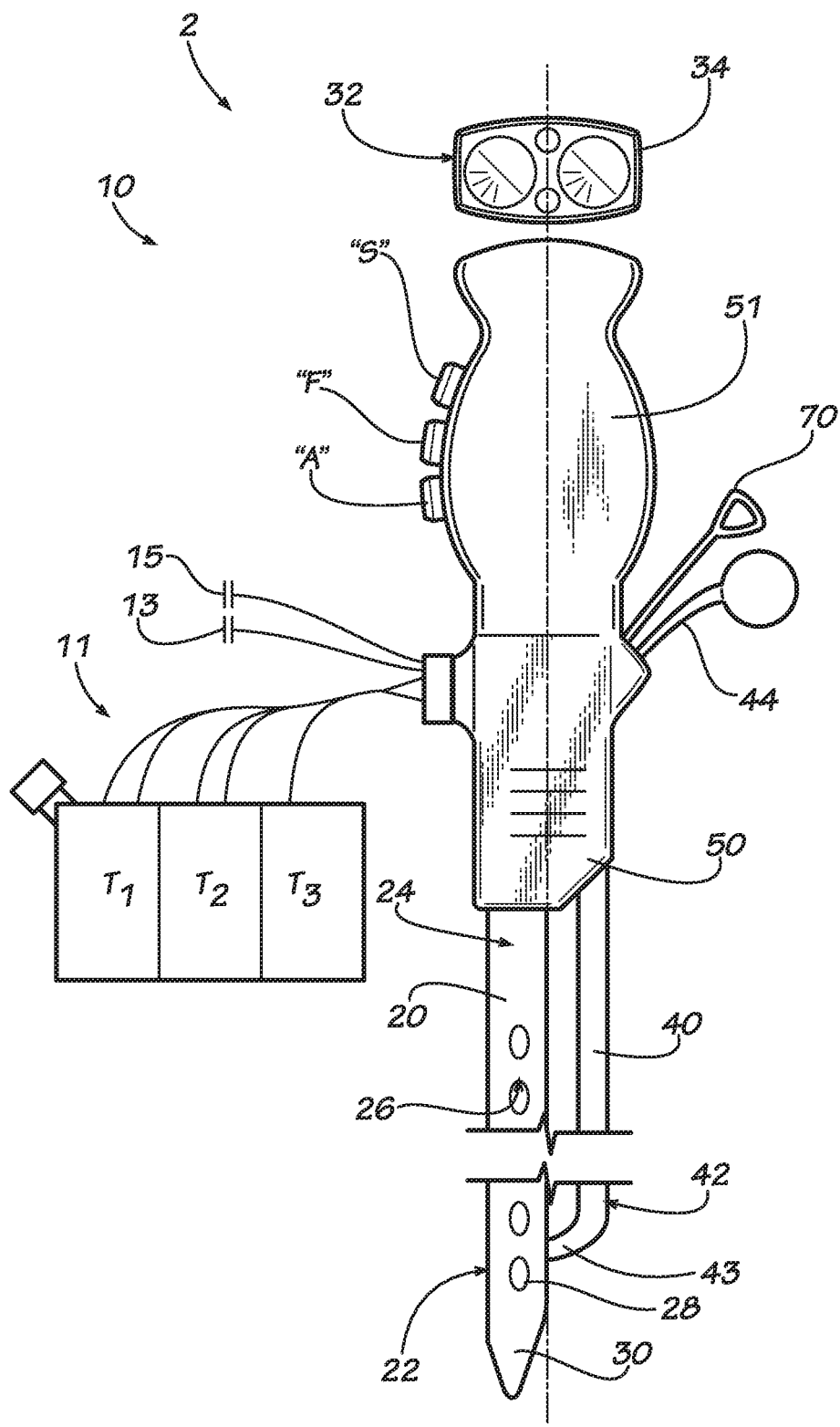
FIG. 1 is a schematic illustration showing a medical device in accordance with an embodiment of the present disclosure.

Embodiments of the present disclosure are detailed below with reference to the drawings in which like reference numerals designate identical or corresponding elements in each of the several views. Throughout this description, the term "proximal" will refer to the portion of the medical device or component thereof that is closest to the mouth of the patient, and the term "distal" will refer to the portion of the medical device or component that is farther along the digestive tract. The term proximal has also been used to refer to the portion of the medical device or component that is generally closest to the user and the term "distal" has been used to refer to the portion of the medical device or component thereof that is generally farthest from the user.

Turning now to FIGS. 1, 2, and 7-9, a surgical system 2 is provided that includes a medical device designated as 10 in accordance with an embodiment of the present disclosure. The medical device 10 is configured for use in resection of gastrointestinal tissue. As an example, the medical device 10 can be used in a sleeve gastrectomy procedure.

The medical device 10 includes an elongated tube 20 and an elongated member 40 coupled to the tube 20. The materials for the tube 20 and the member 40 are generally polymeric materials appropriate for surgical applications, such as the materials used to make a bougie or catheter. The tube 20 is hollow, whereas the member 40 can be hollow or solid. Tube 20 is formed from flexible materials such as silicone and rubber, although other suitable flexible materials are also contemplated. Tube 20 has a distal portion 22 and a proximal portion 24 and defines at least one lumen 26 extending therethrough. A plurality of perforations or openings 28 are defined through an outer wall of distal portion 22 of tube 20. Openings 28 enable fluid communication through the outer wall of tube 20 between lumen 26 and the exterior of tube 20.

Tube 20 further includes a distal end cap 30 disposed at distal portion 22, or is otherwise closed. The distal portion 22 of the tube 20 can be closed in any appropriate manner. Distal end cap 30 may define a rounded tapered configuration, blunt conical configuration, or any other suitable configuration that facilitates atraumatic insertion into a patient's stomach. Distal end cap 30 is affixed to the distal portion 22 of tube 20 to seal off lumen 26 at the distal portion 22 of tube 20. The tube 20 can have a diameter between about 32-42 French.

Figure 7:
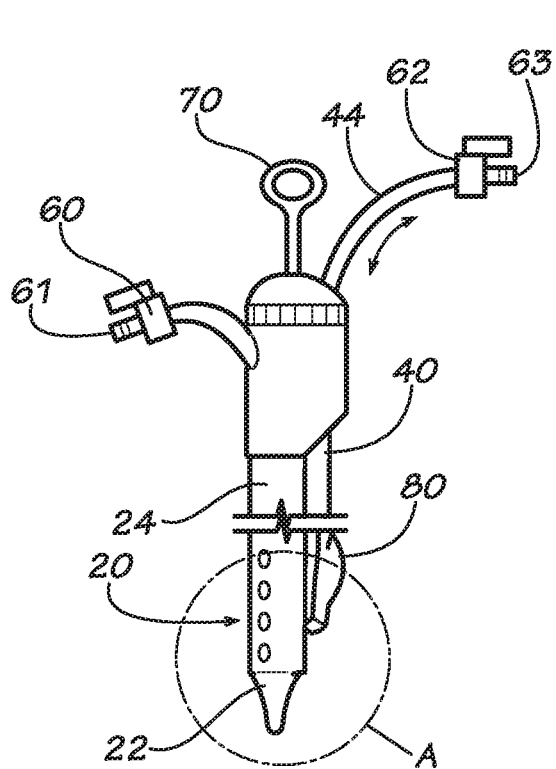
FIG. 7 is a schematic view illustrating a medical device in accordance with another embodiment of the present disclosure.

Tube 20 has an open proximal portion 24 configured to connect to a suction source "S" and a fluid source "F" (see FIG. 1). Suction source "S" is operable to provide suction within lumen 26 for suctioning fluids, stomach contents, etc., through apertures or openings 28 and into lumen 26 for removal and/or for suctioning stomach tissue into contact with tube 20. One or more control members 32, e.g., a valve, may be disposed between tube 20 and the suction source "S" to control the suction force being applied. It is contemplated that controls may alternatively or additionally be provided on a user interface (not shown) of the suction source "S." The medical device 10 has at least a shut off valve 60 at a vacuum port 61, and another shut off valve 62 at a fluid/air supply port 63, at proximal portion 24 of tube 20 (FIG. 7). Fluid source "F" is configured to pump fluid, e.g., water or air, into lumen 26 of tube member 20 and out through apertures 28 into the stomach. Similar to suction source "S," the fluid source "F" may include one or more control members 34 (FIG. 1) to control the flow rate and/or pressure of fluid being pumped through lumen 26 of tube 20, and the vacuum pressure. In some embodiments, the controls may alternatively or additionally be provided on a user interface (not shown) of the fluid source "F."

Continuing with reference to FIG. 1, member 40 is formed from a semi-rigid, resiliently flexible material, e.g., a suitable elastomer, and defines a length greater than the length of tube 20 such that member 40 can be accessed outside the patient and/or remotely of the surgical site. Member 40 has a distal portion 42 having a distal end 43 and a proximal portion 44. Distal end 43 of member 40 is integrally, i.e., monolithically, formed with or otherwise affixed to distal portion 22 or distal end cap 30 of tube 20.

Figure 9:
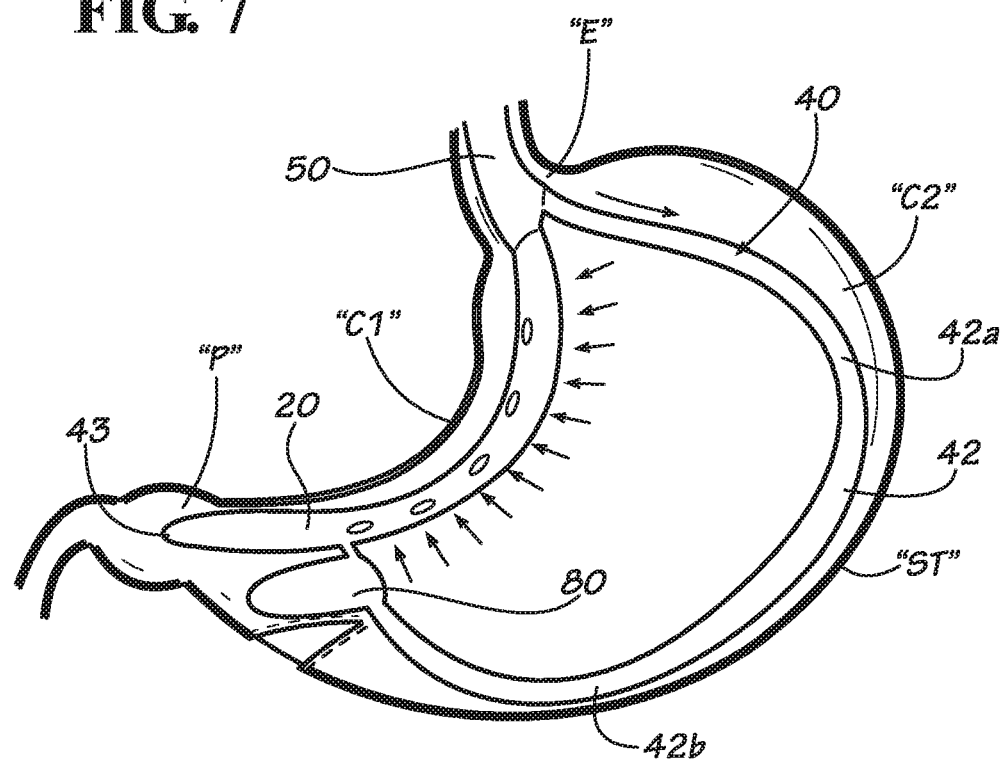
FIG. 9 is a perspective view of the medical device shown in FIG. 7.

A coupling 50, e.g., a ring, sleeve, hook, latch, etc., is affixed to tube 20. Coupling 50 slidably receives the member 40 therethrough to movably or slidably couple member 40 to tube 20 in a position between the distal and proximal ends 22, 24 of tube 20. As a result of the above-configuration, a portion of member 40 is movable or slidable through the coupling 50 and relative to tube 20 between an initial position in which member 40 is disposed alongside tube 20 (see FIG. 1) and deployable to a subsequent position in which member 40 engages a greater curvature of a stomach, as shown, for example, in FIG. 9. In the initial, contracted position of member 40, distal portion 42 of member 40 extends along and abuts the outer surface of the tube 20. In the subsequent, deployed position, the distal portion 42 of member 40 is bowed outwardly from tube member 20, as shown in FIG. 9.

In the deployed position, the member 40 automatically assumes the shape of the greater curvature of the stomach, forming a bulging region 42a and a tapering region 42b due to the pliability of member 40. The member 40 defines a configuration that generally complements the curvature of the greater curvature portion "C2" of the stomach "ST" (see FIG. 9). Preferably, the flexibility and resilience and dimensioning of the member 40 is such that member 40 automatically forms a half-heart shape, with a large, bowed curvature adjacent the proximal portion 44. Such a shape complements the greater curvature of the stomach. These features can be adapted to applications in other hollow organs as well. The member 40 should be strong enough to stretch out the stomach, and reposition the anterior and posterior walls of the stomach.

Proximal portion 44 of member 40 may be grasped and manipulated to move, translate, or slide relative to tube 20 to transition member 40 between the contracted and deployed positions. The member 40 may have an actuator or handle to be grasped and manipulated. As mentioned above, member 40 is dimensioned such that proximal portion 44 is accessible from outside the patient, thus readily enabling manipulation thereof, and allowing proximal portion 44 of member 40 to be moved, translated, or slid downwardly with respect to the tube 20. More specifically, translating member 40 in a distal direction relative to tube member 20 urges member 40 in a distal direction through coupling 50 such that distal portion 42 of member 40 is bowed outwardly relative to tube 20 towards the deployed position. Translating member 40 in a proximal direction relative to tube 20 pulls member 40 proximally through coupling 50 such that the distal portion 42 of member 40 is pulled inwardly relative to tube 20 to the contracted position. As an alternative to manually manipulating rod member 40, an actuator or actuation assembly (not shown) may be coupled to the proximal ends 24, 44 of tube 20 and member 40 to enable selective translation of member 40 relative to tube 20.

Figure 2:
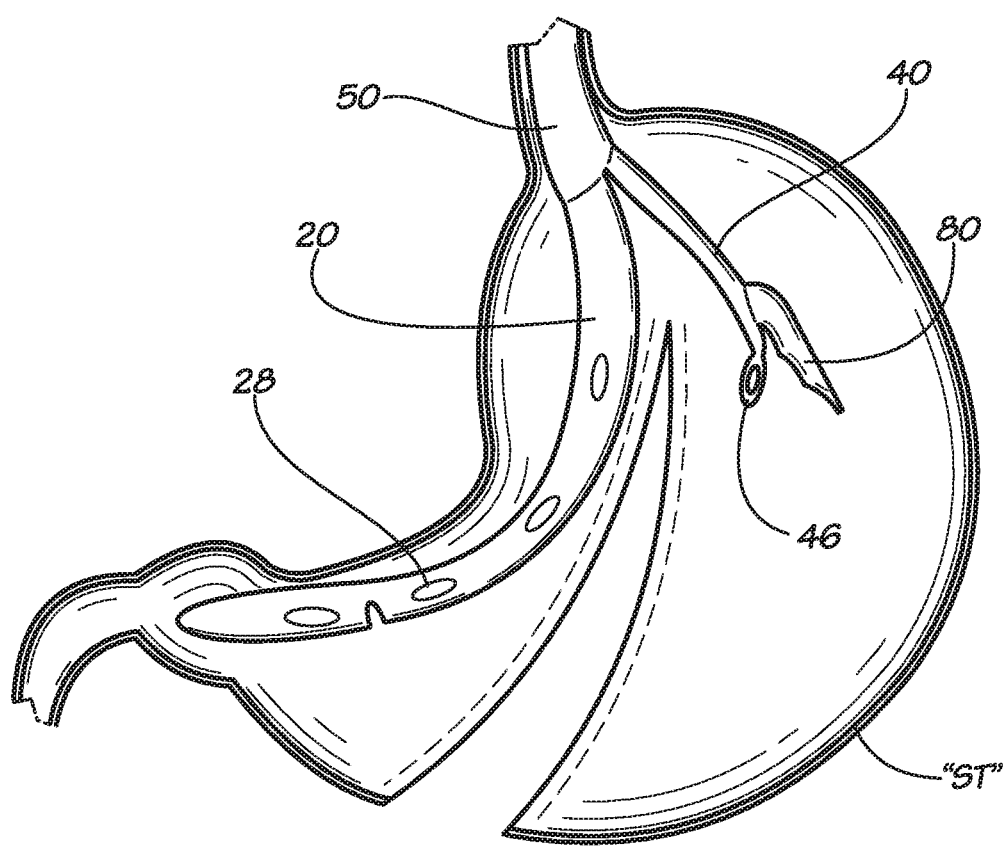
FIG. 2 is a perspective view of an embodiment of a medical device according to the present disclosure, inserted into a stomach.

In any of the embodiments disclosed herein, the distal end 43 of member 40 can include a loop or hook 46 and a hinge 45, as shown in FIG. 7. A release wire or member 70 extends distally toward the distal end 43 and is accessible at the proximal ends 24, 44 of the member 40 and tube 20. The release wire 70 has a distal end 72 that extends through the loop 46, maintaining the connection between the member 40 and the tube 20. The proximal end 44 of the member 40 can have an actuator or handle to facilitate manipulation thereof. The hinge 45 allows the member 40 to be positioned alongside the tube 20. Translating the release wire 70 in a proximal direction frees the member 40 from the tube 20, ensuring that the member 40 can be detached from the tube 20, as shown in FIG. 2, before resection and/or stapling of tissue occurs. In this way, the user of the medical device 10 can avoid stapling the member 40 and leaving part of it within the stomach tissue. Alternatively, the hinge 45 can be a frangible connection that can be broken to allow the member 40 to be removed or detached.

In any of the embodiments disclosed herein, a balloon 80 can be provided as part of the medical device 10, at a distal end of the member 40 (see FIGS. 2, 7-9). The balloon or other expandable element 80 can be inflated using the fluid/air supply mentioned above, or the member 40 can have a separate passageway for this purpose. The balloon 80 can be shaped to complement a portion of the stomach and is disposed on the member 40 so that in the stomach it will be positioned at a specific distance (typically 6 cm) from the pyloric sphincter. This helps to start the transection at the preferred location, which is at a distance of about 6 cm from the sphincter. In addition, the balloon 80 indicates the location of the initial placement of a stapling and cutting device, as discussed further below.

Figure 10:
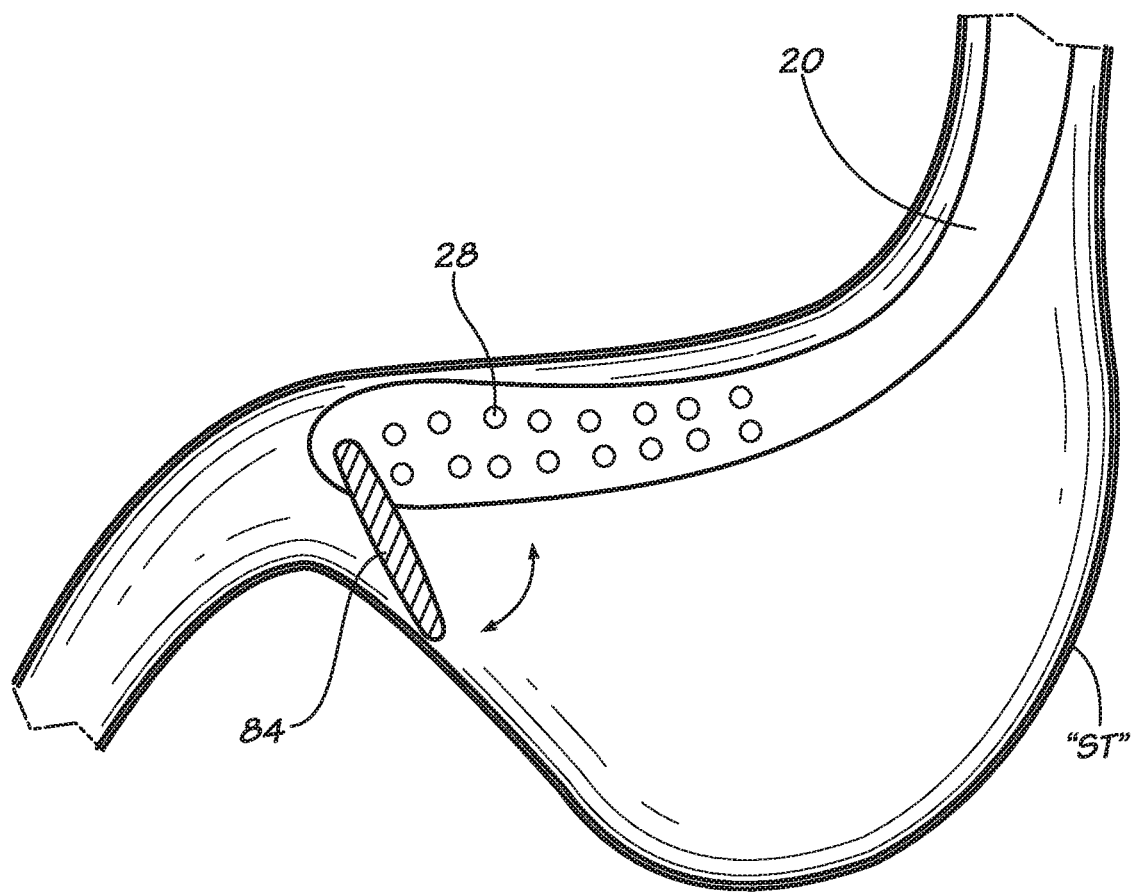
FIG. 10 is a perspective view of a medical device according to another embodiment of the present disclosure, inserted into a stomach.

Alternatively to the balloon 80, an expandable element or a lever 84 may be attached to the member 40 at the distal end 43 of the member 40, as shown in FIG. 10. The lever 84 is pivotable in two directions toward and away from the lesser curvature of the stomach. The lever 84 has an initial position substantially parallel with the tube 20 or member 40, and a deployed, perpendicular or transverse position with respect to the member 40. The lever 84 is actuated by pulling a trigger, pushing a button, or releasing potential energy.

Figure 8:
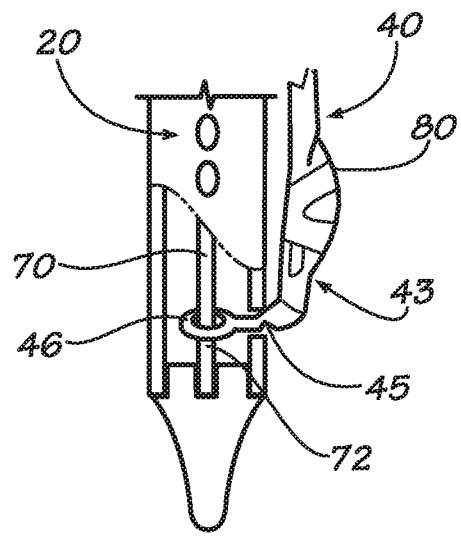
FIG. 8 is a cutaway view of detail A shown in FIG. 7.

Referring to FIGS. 7-9, the use of medical device 10 during the course of a sleeve gastrectomy procedure is described. However, it is also envisioned that medical device 10 be capable of use in other similar surgical procedures, within hollow organs other than the stomach, etc. Initially, with member 40 disposed in the contracted condition, and the balloon or expandable element 80 in an initial, collapsed or deflated position, medical device 10, led by distal end cap 30, is inserted through the patient's mouth, esophagus, and into the patient's stomach "ST." At least distal portion 22 of tube 20, coupling 50, and distal portion 42 of member 40 are disposed within the patient's stomach "ST." Once this position has been achieved, proximal portion 44 of member 40 is translated distally relative to tube 20 such that distal portion 42 of member 40 bows outwardly relative to tube 20 towards the deployed position (see FIG. 9). As distal portion 42 of member 40 bows outwardly towards the deployed position, tube 20 is urged towards and into complementary mating relation with the lesser curvature portion "C1" of the stomach "ST," while distal portion 42 of member 40 is urged towards and into complementary mating relation with the greater curvature portion "C2" of the stomach "ST", engaging and flattening the stomach. As such, the orientation of medical device 10 with tube 20 extending along the lesser curvature portion "C1" of the stomach "ST" between the esophageal sphincter "E" and the pyloric sphincter "P" can be readily achieved. As a result of this configuration of medical device 10 in the deployed position, the above-described orientation of device 10 within the stomach "ST" is maintained despite spasms, folding, spiraling, and/or shifting of the stomach "ST." Further, the configuration of medical device 10 allows for proper positioning within the stomach "ST" without the assistance of a viewing instrument, e.g., an endoscope (see FIG. 6). At this point, the balloon 80 can be inflated, using the fluid/air source, or other source of fluid pressure, to help position the distal portion 22 of tube 20 in or near the pylorus.

Once the proper orientation of tube 20 of medical device 10 has been achieved, suction/vacuum source "S" may be activated to apply suction within lumen 26 for suctioning any remaining contents within the stomach "ST" into lumen 26 of tube 20 through apertures 28. Application of suction within lumen 26 also suctions the lesser curvature portion "C1" of the stomach "ST" to the outer periphery of tube 20, to ensure and maintain the complementary mating relation of tube member 20 with the lesser curvature portion "C1" of the stomach "ST." Control member 32 may be manipulated or otherwise controlled to apply sufficient suction to maintain the relative position of tube 20 without damaging surrounding tissue.

Due to the suction applied to the stomach tissue "ST," the tube 20 and the balloon 80 are visible from the exterior of the stomach. The user of the medical device 10 places a surgical stapling and cutting device adjacent the balloon 80, while avoiding the balloon 80, and fires the stapling and cutting device (see FIG. 9) to make the initial transection. The balloon 80 can then be deflated or otherwise collapsed. Alternatively, lever 84 is used to position the distal portion 22 of the tube 20 with respect to the pyloric sphincter, and/or indicate the initial location of the stapling and cutting device.

The proximal portion 44 of member 40 is then translated proximally relative to tube 20 such the distal portion 42 of member 40 is pulled inwardly relative to tube 20 back to the contracted position. The member 40 is then detached from the tube 40, by pulling on the member 40 to break the frangible connection between distal end 43 of member 40 and distal portion 22 of tube 20, or by moving the release wire 70 to detach the distal end 43 of the member 40 from the distal portion 22 of tube 20. The member 40 is then completely removed from the medical device 10. The shape of the tube 20 is then used as a guide for further cutting and stapling. In this way, a tubular section of stomach tissue is defined.

Transection of the stomach "ST" adjacent tube member 20 on a side of tube member 20 opposite to the lesser curvature portion "C1" of the stomach "ST" may be effected in any suitable fashion, e.g., using a stapling device or other suitable device. Transection in this manner reforms the stomach "ST" to a tubular-shaped configuration (or sleeve) that is slightly larger than the outer dimension of tube 20 and extends between the esophageal sphincter "E" and the pyloric sphincter "P." The suction is maintained while the stomach tissue is transected and stapled. As can be appreciated, the diameter of tube 20 may be selected in accordance with a desired diameter of the tubular-shape reformed stomach. The remaining stomach tissue is removed from the patient.

Figure 5:
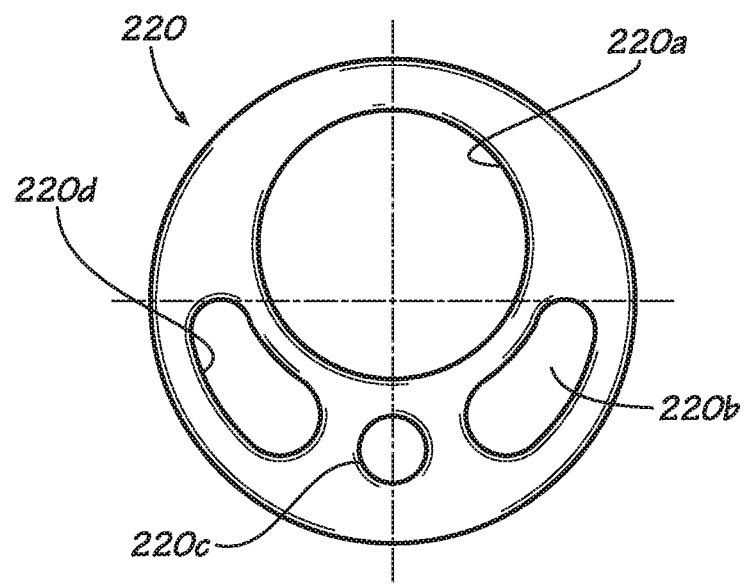
FIG. 5 is a cross-sectional view of a tube of a medical device in accordance with further embodiments of the present disclosure.

Upon completion of the stomach transection, the applied suction is removed and a leak test is performed. The leak test is performed by activating the fluid source "F" to pump fluid through lumen 26 of tube 20 and into the stomach via apertures 28. The fluid may be air, colored water, or other suitable gaseous or liquid leak test agent. The fluid is pumped into the stomach "ST," e.g., via controlling control member 34, to achieve a pressure within the stomach "ST" sufficient to test the transected stomach tissue for extravasation. If extravasation (leakage) is detected, the leak is repaired prior to completing the procedure, by suturing or any other appropriate method. The leak test is repeated after repairing the portion or portions of transected tissue where extravasation is detected, until no further extravasation is detected. Ultimately, medical device 10 is withdrawn from the patient's stomach "ST." A scope can be provided with the medical device 10, and the tube 20 may have a separate passageway for the scope or other devices, as shown in FIG. 5. Alternatively, the user of the medical device 10 may pass a scope through the singular passageway as needed.

In any of the embodiments disclosed herein, the tube 20 can be made of a clear polymer and a scope or camera may be provided. In any of the embodiments disclosed herein, an ultrasound probe can be provided. In any of the embodiments disclosed herein, the release wire or release member 70 can have distance markings provided thereon, to assist the user of the medical device 10 in deploying or retracting these components of the medical device 10.

Figure 3:
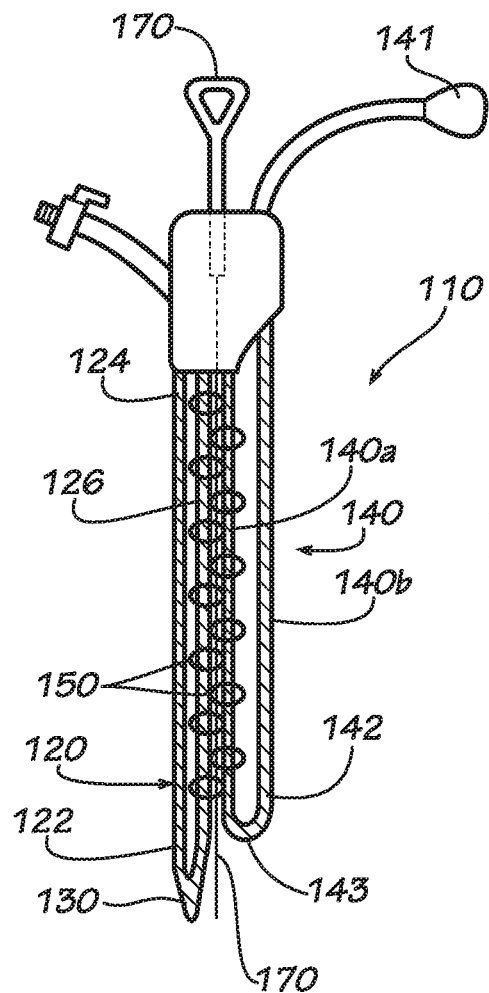
FIG. 3 is a schematic, cutaway view, in part phantom, of a medical device according to another embodiment of the present disclosure.
Figure 4:
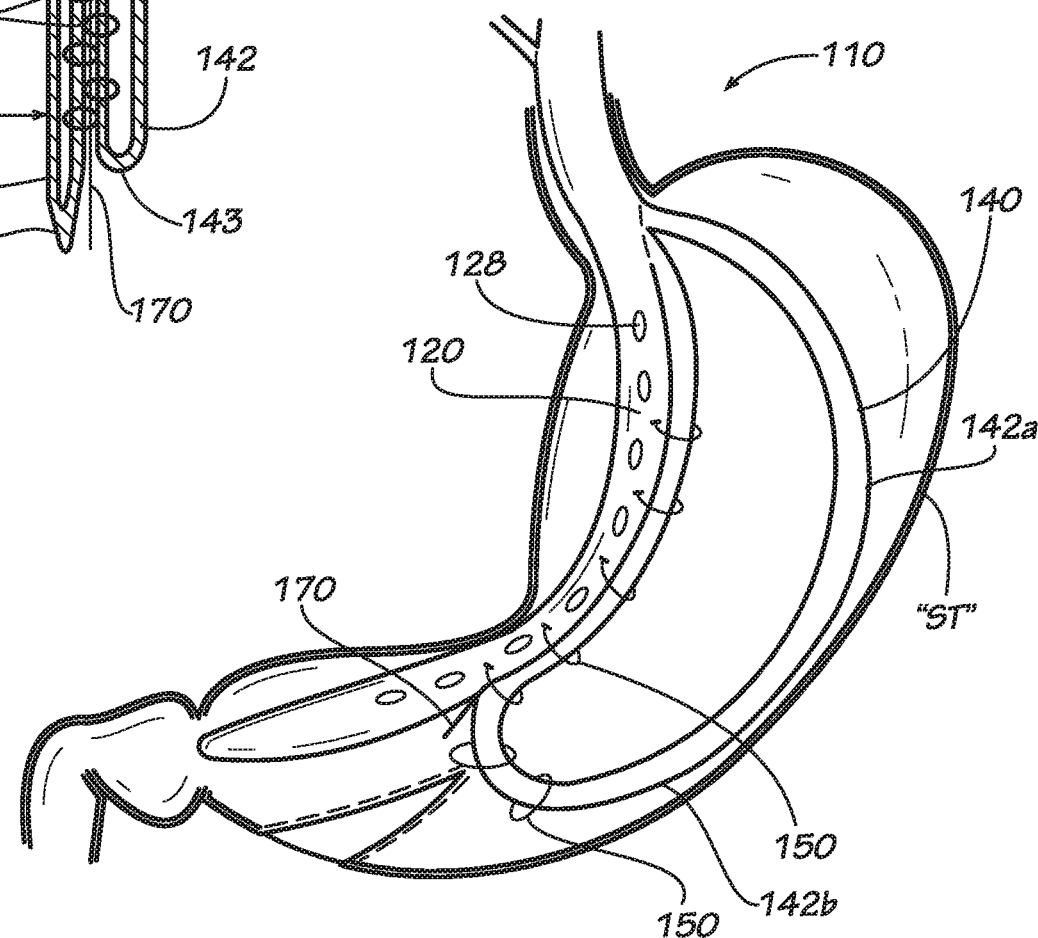
FIG. 4 is a perspective view of the medical device shown in FIG. 3, inserted into a patient's stomach.

With reference to FIGS. 3 and 4, in a further embodiment of the present disclosure, a medical device 110, similar to medical device 10 discussed above, is provided. Medical device 110 includes a member 140, similar to member 40 discussed above, coupled to a tube 120, similar to tube 20 discussed above. The materials for the tube 120 and the member 140 are similar to those discussed above with reference to tube 20 and member 40.

Tube 120 has a distal portion or distal end 122 and a proximal portion or proximal end 124 and defines at least one lumen 126 extending therebetween. A plurality of perforations or openings 128 enable fluid communication through an outer wall of tube 120 for the application of suction and/or fluid. Tube 120 further includes a closed distal end, similar to tube 20 discussed above. Tube 120 has an open proximal end configured to connect to a suction source and a fluid source. One or more control members (not shown), e.g., a valve, may be disposed between tube member 120 and the suction source to control the suction force being applied. In some embodiments, controls may alternatively or additionally be provided on a user interface (not shown) of the suction source. The medical device 110 has valves for each of the vacuum port and fluid/air supply port.

Continuing with reference to FIGS. 3 and 4, member 140 is formed from a semirigid, resiliently flexible material, and defines a distal portion 142 having a distal end 143 and a proximal portion 144. The member 140 is connected to the tube 120 through a coupling device, such as, for example, a series of couplings 150 that can be configured as rings, sleeves, hooks, latches, etc. For example, the couplings 150 can be pieces of suture. The couplings 150 allow a gradual detachment of the member 140 from the tube 120 to help keep the stomach in a flat configuration. Member 140 has a U-shaped configuration, with a first leg 140*a* of the member 140 attached to the tube 120 by couplings 150. Couplings 150 are in the form of small suture loops inserted through small slits in the leg 140*a* of the member 140 and about release wire 170. A second leg 140*b* extends freely toward the proximal end 144. The couplings 150 can be breakable or otherwise releasable, or they can have a release wire 170 passed through each of the couplings 150.

The member 140 is gradually detachable by retracting the release wire 170. In some embodiments, the couplings 150 can be bioabsorbable or an otherwise medically acceptable material. In the initial, contracted position of the member 40, distal portion 142 of member 140 extends along and abuts the outer surface of the tube 120, and in the subsequent, deployed position, the distal portion 142 of member 140 is bowed outwardly (see FIG. 4) from tube member 120. The member 140 is gradually deployed, as discussed above, by translating the second leg 140*b* with respect to the tube 120. As member 140 is moved to the deployed position, member 140 automatically assumes the shape of the greater curvature of the stomach by forming a bulging region 142*a* and a tapering region 142*b*. The member 140 defines a configuration that generally complements the curvature of the greater curvature of the stomach. Preferably, the flexibility and resilience and dimensioning of the member 140 is such that member 140 automatically assumes the shape of the greater curvature of the stomach.

An actuator or handle 141 of proximal portion 144 of member 140 may be grasped and manipulated to position the member 140 with respect to the tube 120. Member 140 is dimensioned such that proximal portion 144 is accessible from outside the patient.

The release wire or member 170 extends distally toward the distal end 143 and is accessible at the proximal ends 124, 144 of the tube 120 and member 140. The release wire 170 extends through each coupling 150, maintaining the connection between the member 140 and the tube 120. Translating the release wire 170 in a proximal direction gradually frees the member 140 from the tube 120 by severing or detaching couplings 150, ensuring that the member 140 can be removed from the tube 120 before the resection and/or stapling of tissue occurs. Alternatively, couplings 150 can be a frangible connection that can be broken to allow the member 140 to be removed.

The procedure is performed in a manner similar to that discussed above with regard to medical device 10, with the member 140 being detached from the tube 120 before the stapling and cutting of tissue occurs. The suction is maintained to stabilize the tissue and maintain tube 120 in abutment or in close proximity with the inner curvature of the stomach and the tube 120 is used as a guide for the stapler.

Figure 11:
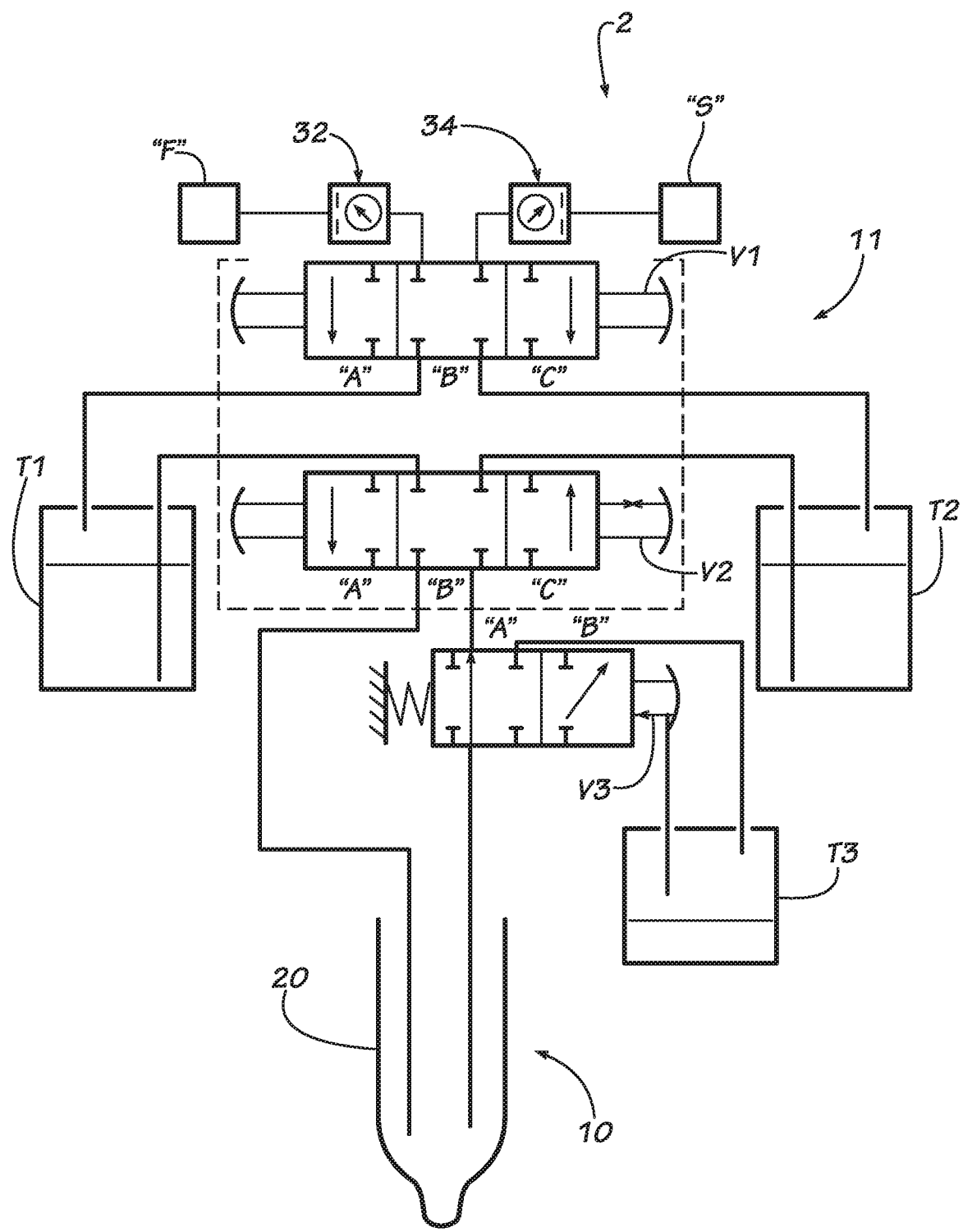
FIG. 11 is a schematic view of a system for controlling a medical device according to another embodiment of the present disclosure.

With reference to FIG. 11, it is contemplated that, in any of the embodiments disclosed herein, a reusable portion is provided to form a system 2 that controls the suction and fluid/air source of any of the medical devices disclosed herein. For example, as shown in FIGS. 1 and 11, system 2 includes medical device 10 and a reusable portion 11. Reusable portion 11 includes a tank T1 having a fresh supply of saline or water while a tank T2 can collect the used saline or water. A tank T3 serves as a filter as the stomach volume is equalized with atmospheric pressure. There is a pressure line 13, vacuum line 15, and atmospheric line "A" leading to the medical device 10. The air pushes saline from the tank T1 to the stomach and its pressure can be monitored and regulated. Valve V1 and valve V2 interact with the lines 13 and 15, respectively, so that the air pressure line 13 is connected to tank T1 and the air pressure pushes saline to the stomach until a predetermined pressure is reached. Valve V1 and valve V2 are normally biased to a closed position "B" in which both pressure and vacuum valves V1, V2 are closed. Valves V1 and V2 are activated together.

Valves V1, V2 and a release valve V3 have three positions: "A", "B", and "C." Release valve V3 is normally biased to the "A" position, which allows the vacuum line 15 to be connected. When valve V1 and valve V2 are urged to position "A" the stomach will be pressurized with fluid to check for leaks. When valve V1 and valve V2 are moved to position "C," the vacuum source "S" will remove air and fluid from the stomach. Finally, moving valve V3 to the "B" position allows the internal stomach pressure to equalize with atmospheric pressure.

A safety feature is contemplated, either a mechanical or computerized control, or both, in which valve V3 is only activated if valve V1 and valve V2 are in their closed "B" positions. In system 2, all parts used in the patient are single patient use only, and the pre-filled tanks and valves, etc., are reusable. These portions of the system 2 can be coupled in an appropriate manner, such as via bayonette couplings. Appropriate control buttons (see FIG. 1) can also be provided.

The medical device 10 shown in FIG. 1 can have reusable and sterilizable portions, such as, for example, a handle 51. The handle 51, with buttons for controlling the suction, fluid supply, valves and pressure regulation, is sterilizable and reusable, whereas the remainder of the medical device 10 is discarded after use. The medical device 10 has a port or ports for attachment to a source of saline, a used saline reservoir, and a tank at atmospheric pressure.

Figure 6:
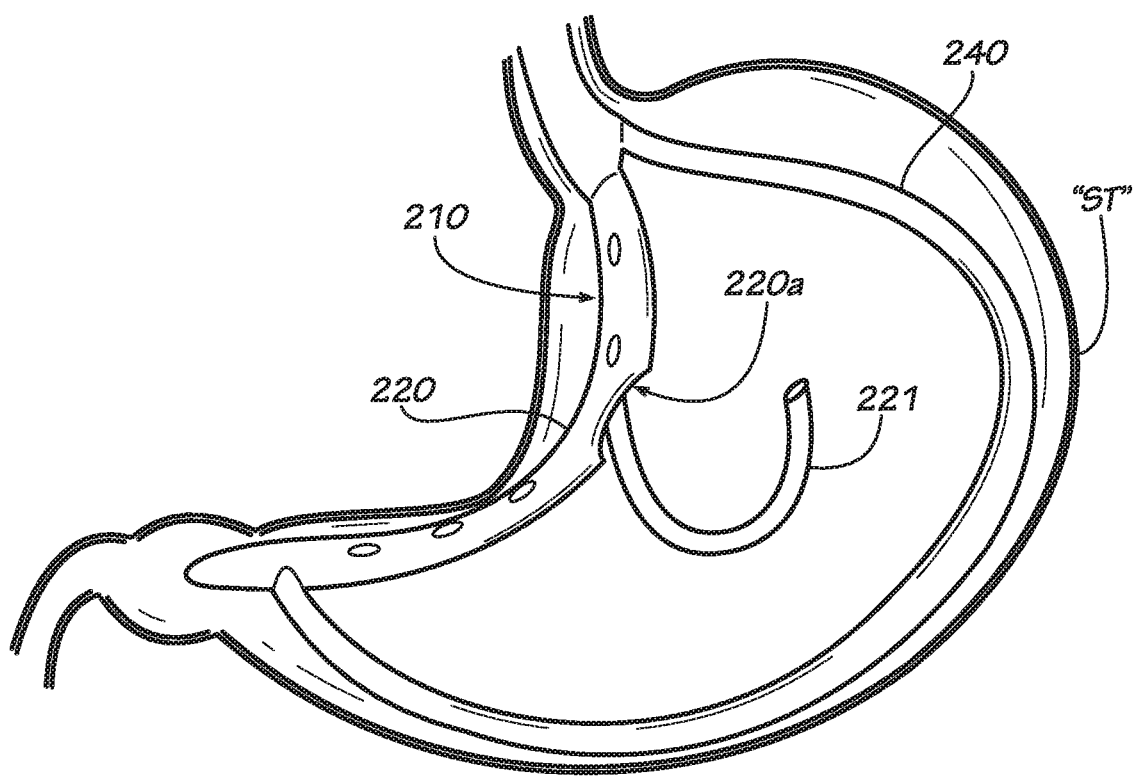
FIG. 6 is a perspective view of a medical device according to another embodiment of the present disclosure, inserted into a stomach.

In another embodiment, as shown in FIGS. 5 and 6, a medical device 210, similar to medical devices 10 and 110 described above, is provided. Medical device 210 includes a tube 220, similar to tube 20 discussed above, and a flexible member 240, similar to flexible member 40 discussed above, movably, slidably or translatably coupled thereto. Tube 220 has an aperture or endoscopic lumen 220*a* for the passage of a scope 221 through the tube 220 and into the stomach, as shown in FIG. 6. Tube 220 also includes a vacuum lumen 220*b*, a release wire lumen 220*c*, and a leak test fluid lumen 220*d*, or any combination thereof.

Figure 12:
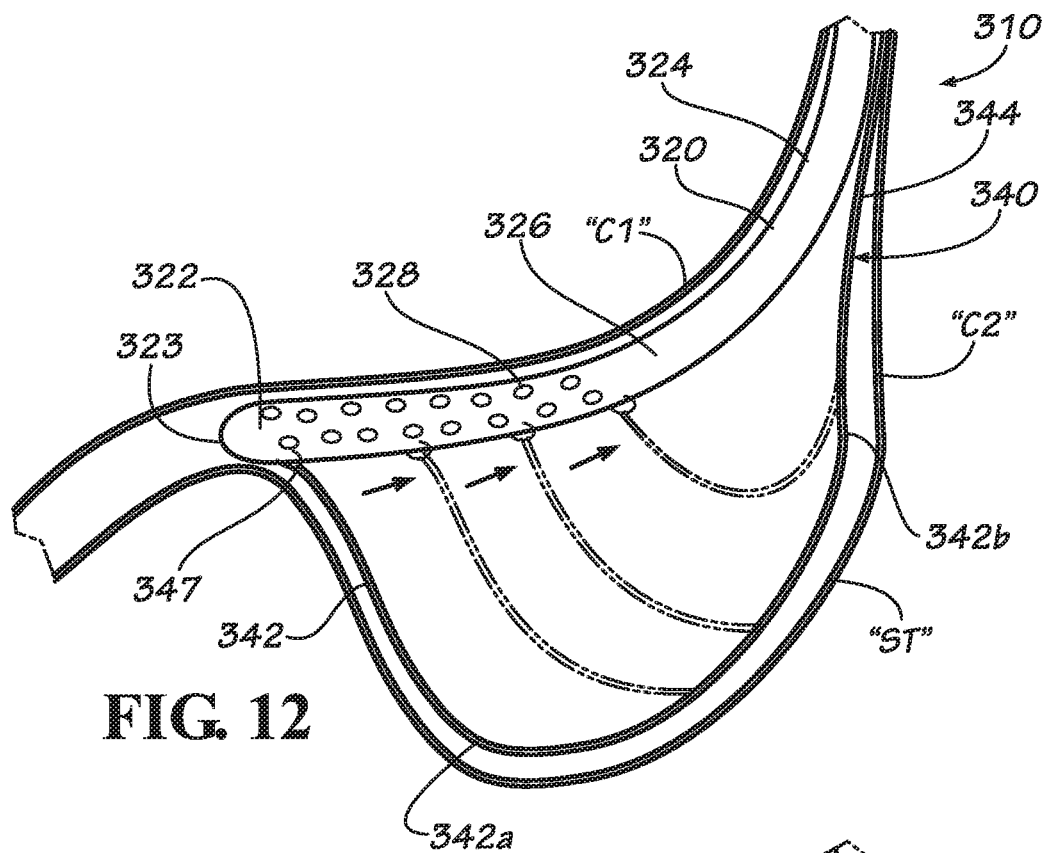
FIG. 12 is a perspective view, in part phantom, of a medical device according to another embodiment of the present disclosure, with the member in a pre-deployed position.
Figure 13:
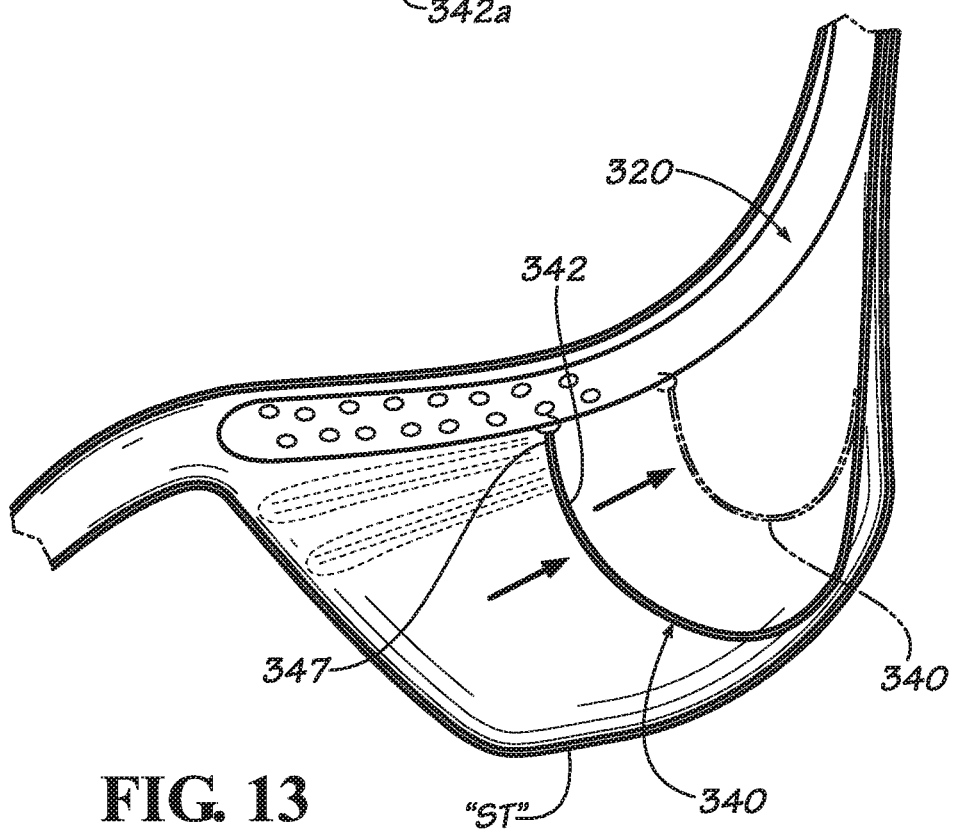
FIG. 13 is a perspective view, in part phantom, of the medical device shown in FIG. 12, with the member in a retracted position.

In another embodiment of the present disclosure, as shown in FIGS. 12 and 13, a medical device 310, similar to medical device 10 discussed above, is provided. Medical device 310 includes a member 340, similar to member 40 discussed above, and a tube 420, similar to tube 20 discussed above. Member 340 has a distal end 347 that is slidably connected with tube 320. Tube 320 is coupled to member 340 and deployable therefrom. Tube 320 has a distal portion 322 and a proximal portion 324 and defines at least one lumen 326 extending therethrough. Tube 320 includes a plurality of perforations or openings 328 configured to enable fluid communication through the outer wall of tube 320 for the application of suction and/or fluid. Tube 320 further includes a closed distal tip 323.

Tube 320 has an open proximal end (not shown) configured to connect to a suction source and a fluid source. One or more control members, e.g., a valve, may be disposed between tube 320 and the suction source to control the suction force being applied. In some embodiments, controls may alternatively or additionally be provided on a user interface (not shown) of the suction source. The device 310 has valves for each of the vacuum port and fluid/air supply port.

Member 340 is formed from a semirigid, resiliently flexible material, and defines a distal portion 342 having a distal end 347 and a proximal portion 344. The member 340 is movably, translatably or slidably connected to the tube 320. Distal end 347 may be slidably connected to a track of tube 320. Proximal portion 344 of member 340 may be grasped and manipulated to position the member 340 with respect to the tube 320, and the member 340 may have an actuator or handle (not shown) for this purpose. As mentioned above with regard to medical device 10, member 340 is dimensioned such that proximal portion 344 is accessible from outside the patient.

Figure 14:
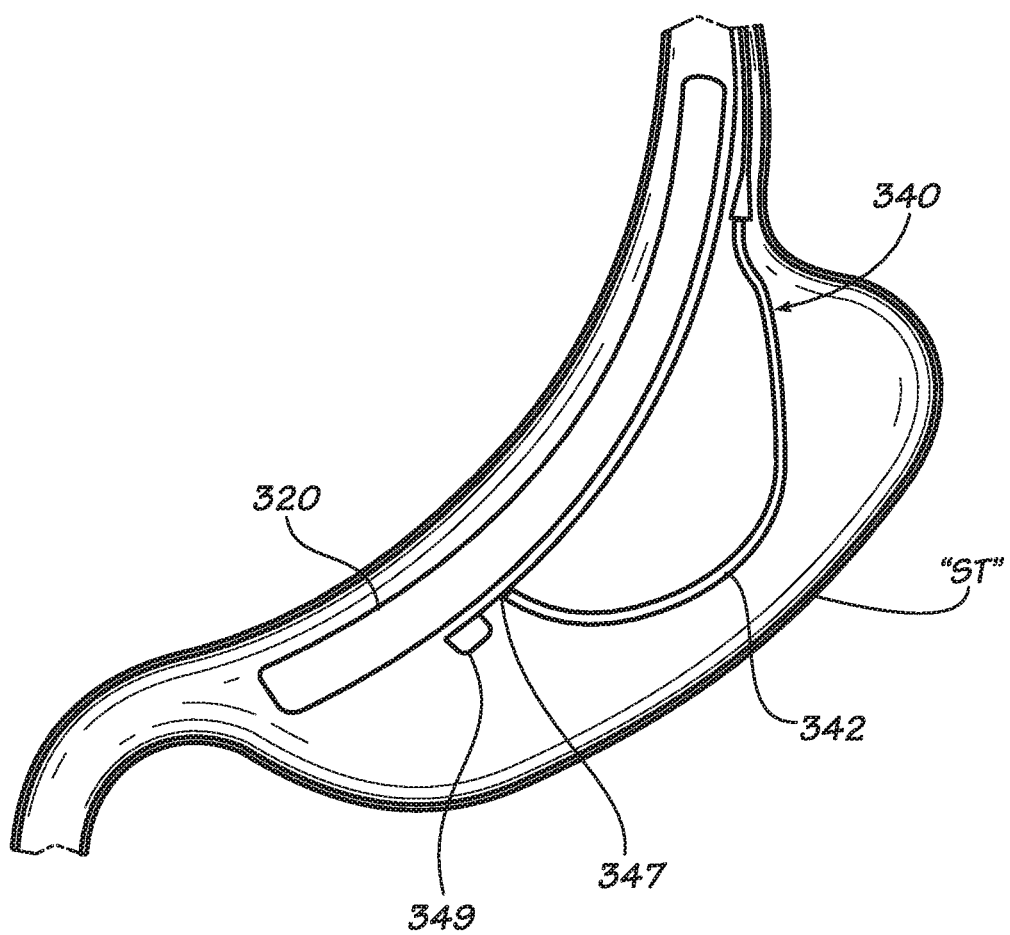
FIG. 14 is a perspective view of a medical device in accordance with another embodiment of the present disclosure, with the member and scope shown in a retracted position.

After the member 340 has been deployed in a manner similar to that discussed above with regard to member 40 of medical device 10, the member 340 is gradually retracted by pulling on an actuator to retract the distal portion 342 of the member 340 with respect to the tube 320. In the initial, contracted position of the member 340, as shown in FIG. 13, distal end 347 of member 340 is disposed with a proximal portion of tube 320. In the subsequent, deployed position, as shown in FIG. 12, distal end 347 is disposed with distal end 322 of tube 320 such that distal portion 342 of member 340 is bowed outwardly from tube member 320. The member 340 is gradually retracted by translating the distal end 347 of member 340 in the proximal direction with respect to the tube 320. Maintaining a deployed position, the member 340 automatically assumes the shape of the greater curvature of the stomach to form a bulging region 342a and a tapering region 342b. It is contemplated that the member 340 can be attached to a vision device, such as, for example, a scope 349 (see FIG. 14) that is slidably attached to the tube 320.

The procedure is performed similar to that discussed above with regard to medical device 10, with the member 340 being readjusted with respect to the tube 320, as the stapling and cutting of tissue occurs. In other words, the distal end 347 of the member 340 is pulled in a proximal direction, and then the tissue is stapled and cut. The distal end 347 of member 340 is further pulled in a proximal direction and then the tissue is again stapled and cut. The procedure proceeds in this manner until the desired tubular section of stomach is formed. The suction is maintained to stabilize the tissue and maintain tube 320 in abutment with a smaller curvature of stomach "ST," and the tube 320 is used as a guide for the stapler.

Figure 15:
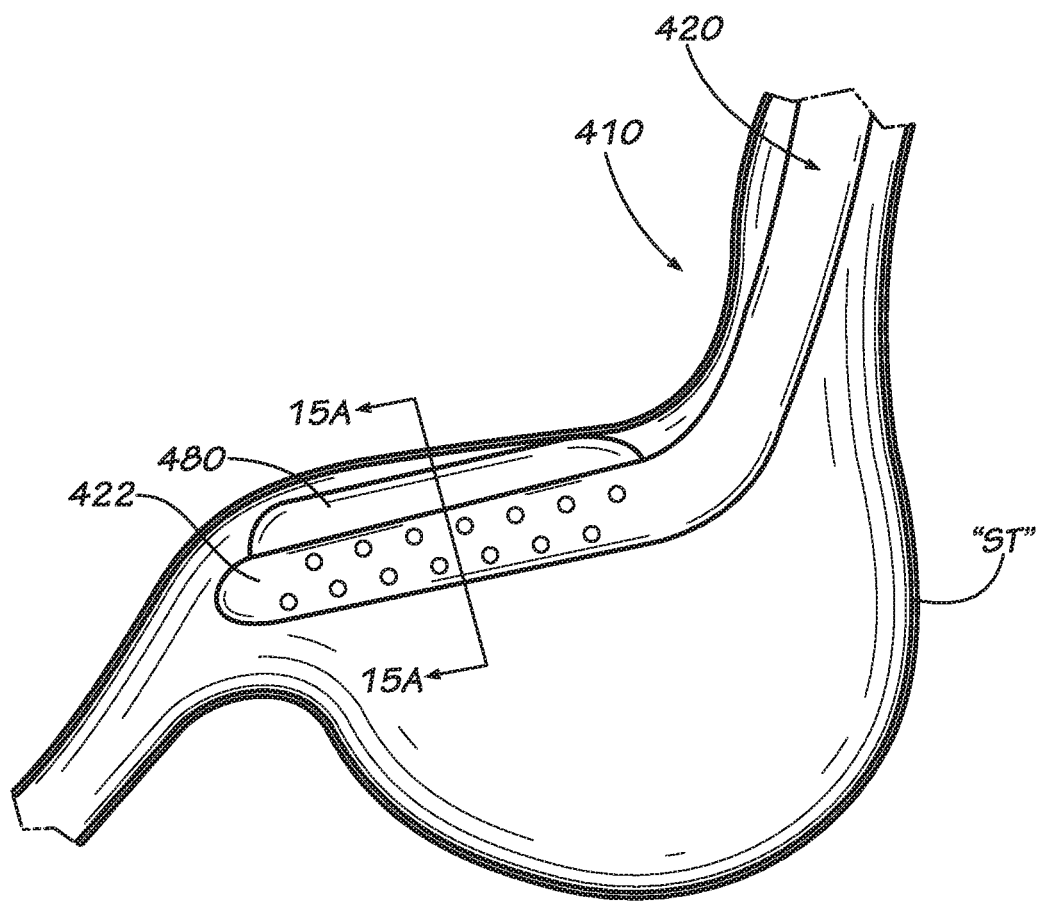
FIG. 15 is a perspective view of a medical device in accordance with another embodiment of the present disclosure.
Figure 15A:
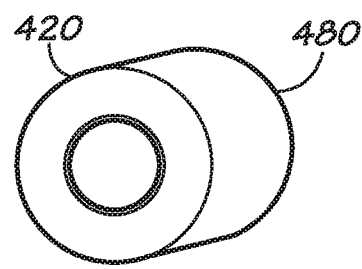
FIG. 15A is a cross-sectional view taken across line 15A-15A in FIG. 15.

In a further embodiment of the present disclosure, as shown in FIGS. 15, 15A, a medical device 410, similar to medical device 10 described above, is provided. Medical device 410 includes a flexible, hollow tube 420, similar to tube 20 described above, and a flexible member 440, similar to flexible member 40 described above, movably, slidably or translatably coupled thereto. Medical device 410 further includes a balloon or other expandable device 480 disposed with a distal portion 422 of tube 420. In this way, an effective size of the medical device 410 can be adjustably expanded.

Balloon 480 can be provided in any of the embodiments disclosed herein, and can be used additionally or alternatively to the balloon 80 discussed above. Using balloon 480, the user of the medical device 410 can provided with a larger or smaller tubular section of stomach in the gastrectomy (see FIG. 15A).

In further embodiments, as shown in FIGS. 16A-16E, 17 and 18, tubes 520, 620, 720, 820, 920, each similar to tube 20 described above, can be configured to have a cross-sectional shape that will reduce the pressure on tissue, such as, for example, stomach tissue "ST," while stapling and cutting occurs. As shown in FIGS. 16A-16E, the cross-sectional shape can be a solid circular core, cylindrical, oval, triangular, diamond, elliptical, etc., to reduce the pressure on the stomach tissue "ST." It is contemplated that any tube disclosed herein can be variously shaped in accordance with FIGS. 16A-16E.

Figure 19A:
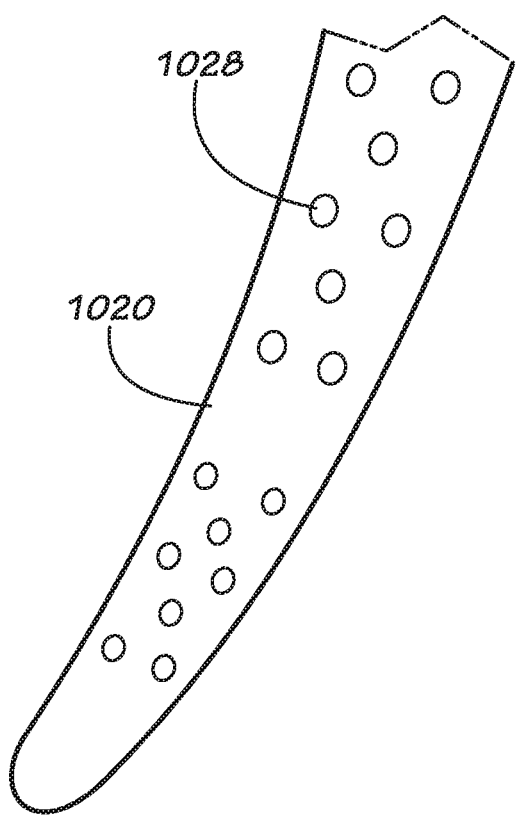
FIG. 19A is a schematic view of a tube of a medical device according to another embodiment of the present disclosure.
Figure 19B:
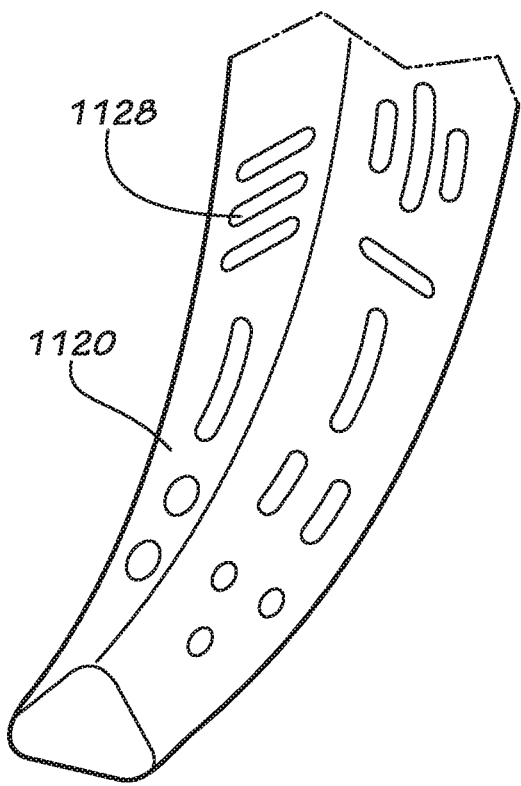
FIG. 19B is a schematic view of a tube of a medical device according to a further embodiment of the present disclosure.

In further embodiments, as shown in FIGS. 19A and 19B, tubes 1020, 1120, similar to tube 20 described above, is provided. It is contemplated that tubes 1020, 1120 can be a component of any medical device described herein. Each of tubes 1020, 1120 includes openings or apertures 1028, 1128, respectively, along a length thereof. Apertures 1028, 1128 can have different density and size, distributed across tubes 1020, 1120. It is envisioned that apertures 1028, 1128 can be distributed across any one of tubes 20, 120, 220, 320, 420. The shape may vary according to the location of the openings, and can be elliptical slots, circular or other shapes.

Figures 20A, 20B, 20C:
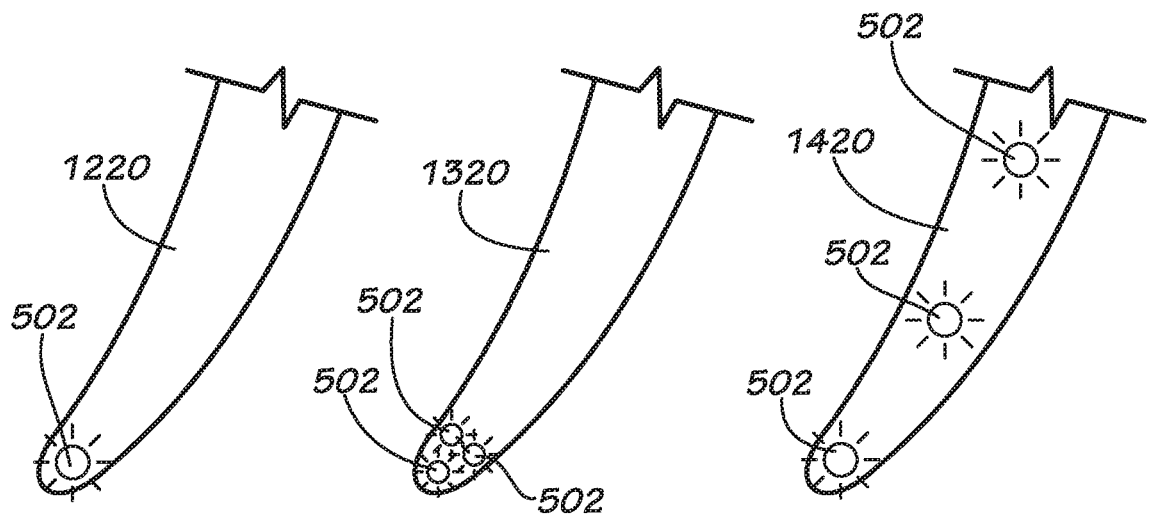
FIGS. 20A through 20C are schematic views of tubes of a medical device according to embodiments of the present disclosure.

In further embodiments, as shown in FIGS. 20A-20C, tubes 1220, 1320 and 1420, similar to tube 20, are provided. Tubes 1220, 1320 and 1420 may include LEDs or other lights 502 disposed within or on an outer surface thereof. Lights 502 can be disposed on the distal ends of the tubes 1220, 1320, 1420, and/or distributed across their length so that the tubes 1220, 1320, 1420 are visible through stomach tissue. It is contemplated that one or more lights 502 can be provided on or within any one of the tubes or other components of the medical devices described herein.

Figure 21:
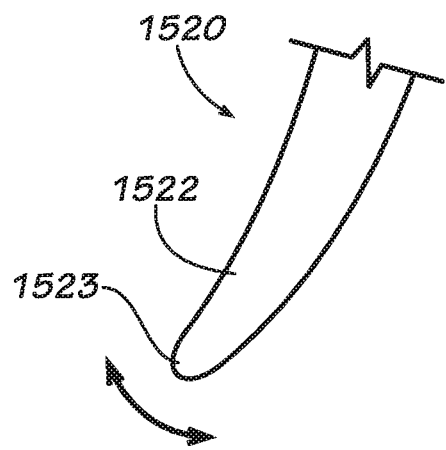
FIG. 21 is a schematic view of a tube of a medical device according to embodiments of the present disclosure.

In one embodiment, as shown in FIG. 21, a tube 1520, similar to tube 20, is provided. A distal end 1522 of tube 1520 may include a vibrating tip 1523 so that it is more readily located with respect to the stomach tissue during vibration thereof. It is contemplated that any one of the tubes described herein can have a vibrating tip.

It will be understood that various modifications may be made to the embodiments of the present disclosure herein. Therefore, the above description should not be construed as limiting, but merely as exemplifications of embodiments. Those skilled in the art will envision other modifications within the scope and spirit of the present disclosure.

Certain aspects of the present disclosure are described in the following numbered paragraphs:

1. A medical device, comprising: a flexible hollow tube extending from a proximal end to a distal end and defining a channel therebetween, a series of openings being defined in a distal portion of the tube allowing for fixation of tissue using suction; a flexible member having an initial position disposed alongside the tube and being deployable to a subsequent position in which the flexible member engages a greater curvature of a stomach, the application of suction placing the tube along a lesser curvature of a stomach, fixing anterior and posterior walls of a stomach, and preventing their movement, the tube being visible under stomach tissue, the flexible member being configured to be deployable to automatically assume a shape of a greater curvature of a stomach, the flexible member including a bulging region and a tapering region when deployed, wherein the flexible member is releasably attached to the distal end of the tube.

2. The medical device according to paragraph 1, wherein the proximal end of the tube is open.

3. The medical device according to paragraph 1, wherein the distal portion of the tube is tapered.

4. The medical device according to paragraph 1, further comprising a release wire for separating the flexible member from the tube.

5. The medical device according to paragraph 1, wherein a distal end of the flexible member includes a balloon.

6. The medical device according to paragraph 5, wherein the balloon is shaped to position the flexible member in the stomach.

7. The medical device according to paragraph 1, wherein the flexible member includes a hinge adjacent a distal end of the flexible member.

8. The medical device according to paragraph 1, wherein the flexible member is selected from the group consisting of a rod and a tube.

9. The medical device according to paragraph 8, wherein the flexible member is made of a flexible resilient material.

10. The medical device according to paragraph 9, wherein the flexible member has a distal end attached to the distal end of the tube, and a proximal end manipulable from outside a patient's body.

11. The medical device according to paragraph 1, further comprising a coupling device that holds the flexible member to the tube.

12. The medical device according to paragraph 11, wherein the coupling device slidably attaches an intermediate portion of the flexible member to an intermediate portion of the tube.

13. The medical device according to paragraph 1, wherein the flexible member is deployable to align a stomach by evening out anterior and posterior walls of a stomach and by pushing the tube and the openings in the tube towards a lesser curvature of a stomach.

14. The medical device according to paragraph 1, wherein the proximal end of the tube is configured for connection to a suction source.

15. The medical device according to paragraph 1, wherein the tube has a cross-sectional shape selected from the group consisting of triangular, diamond, elliptical, and tapered.

16. The medical device according to paragraph 1, wherein at least one of the tube or the flexible member includes at least one illumination device.

17. The device according to paragraph 1, wherein at least one of the tube or the flexible member includes a vision device.

18. A medical device, comprising: a flexible hollow tube extending from a proximal end to a distal end and defining a channel therebetween, a series of openings being defined in a distal portion of the tube allowing for fixation of tissue using suction; a flexible member having an initial position disposed alongside the tube and deployable to a subsequent position in which the flexible member engages a greater curvature of a stomach, the application of suction placing the tube along a lesser curvature of a stomach, fixing anterior and posterior walls of a stomach, and preventing their movement, the tube being visible under stomach tissue, the flexible member being configured to be deployable to automatically assume a shape of a greater curvature of a stomach, the flexible member including a bulging region and a tapering region when deployed, wherein the flexible member has multiple attachments to the tube, the attachments being distributed down a length of the tube.

19. The medical device according to paragraph 18, wherein the flexible member includes a distal end releasably attached to the distal end of the tube.

20. The medical device according to paragraph 18, further comprising a release wire for separating the flexible member from the tube at the attachments.

21. The medical device according to paragraph 18, wherein a distal end of the flexible member includes a balloon.

22. The medical device according to paragraph 21, wherein the balloon is shaped to position the flexible member in a stomach.

23. The medical device according to paragraph 18, wherein the flexible member is selected from the group consisting of a rod and a tube.

24. The medical device according to paragraph 23, wherein the flexible member is made of a flexible resilient material.

25. The medical device according to paragraph 18, wherein the flexible member has a distal end attached to the distal end of the tube, and a proximal end manipulable from outside a patient's body.

26. The medical device according to paragraph 18, further comprising a coupling device that holds an intermediate portion of the flexible member to the tube.

27. The medical device according to paragraph 18, wherein the flexible member is deployable to align a stomach by evening out anterior and posterior walls of a stomach and by pushing the tube and the openings of the tube towards a lesser curvature of a stomach.

28. The medical device according to paragraph 18, wherein the proximal end of the tube is configured for connection to a suction source.

29. The medical device according to paragraph 18, wherein the tube has a cross-sectional shape selected from the group consisting of triangular, diamond, elliptical, and tapered.

30. The medical device according to paragraph 18, wherein at least one of the tube or the flexible member includes at least one illumination device.

31. The medical device according to paragraph 18, wherein at least one of the tube or the flexible member includes a vision device.

32. A medical device, comprising: a flexible hollow tube extending from a proximal end to a distal end and defining a channel therebetween, a series of openings being defined in a distal portion of the tube allowing for fixation of the tube to tissue using suction; a flexible member having an initial position disposed alongside the tube and being deployable to a subsequent position in which the flexible member engages a greater curvature of a stomach, the application of suction placing the tube along a lesser curvature of a stomach, fixing anterior and posterior walls of a stomach, and preventing their movement, the tube being visible under stomach tissue, the flexible member being configured to be deployable to automatically assume a shape of a greater curvature of a stomach, the flexible member including a bulging region and a tapering region when deployed; and an expandable element disposed alongside the distal portion of the tube.

33. The medical device according to paragraph 32, wherein the expandable element is an inflatable balloon, the balloon being inflatable to enlarge an effective diameter of the medical device.

34. The medical device according to paragraph 32, wherein the expandable element is a lever pivotally attached to the distal end of the tube.

35. The medical device according to paragraph 34, wherein the lever can be pivotable in two directions.

36. The medical device according to paragraph 32, wherein the proximal end of the tube is open.

37. The medical device according to claim 32, wherein the distal end of the tube is tapered.

38. The medical device according to paragraph 32, further comprising a release wire for separating the flexible member from the tube.

39. The medical device according to paragraph 32, wherein the expandable element is visible through stomach tissue.

40. The medical device according to paragraph 32, wherein the expandable element is positioned to indicate a location for an initial stapling and/or cutting operation.

41. The medical device according to paragraph 32, wherein the flexible member is selected from the group consisting of a rod and a tube.

42. The medical device according to paragraph 41, wherein the flexible member is made of a flexible resilient material.

43. The medical device according to paragraph 32, wherein the flexible member has a distal end attached to the distal end of the tube, and a proximal end manipulable from outside a patient's body.

44. The medical device according to paragraph 32, further comprising a coupling device that holds the flexible member to the tube 45. The medical device according to paragraph 44, wherein the coupling device slidably attaches an intermediate portion of the flexible member to an intermediate portion of the tube.

46. The medical device according to paragraph 32, wherein the flexible member is deployable to align a stomach by evening out anterior and posterior walls of a stomach and by pushing the tube and the openings of the tube towards a lesser curvature of a stomach.

47. The medical device according to paragraph 32, wherein the proximal end of the tube is configured for connection to a suction source.

48. The medical device according to paragraph 32, wherein the tube has a cross-sectional shape selected from the group consisting of triangular, diamond, elliptical, and tapered.

49. The medical device according to paragraph 32, wherein at least one of the tube or the flexible member has at least one illumination device.

50. The medical device according to paragraph 32, wherein at least one of the tube or the flexible member has a vision device.

51. A medical device, comprising: a flexible hollow tube extending from a proximal end to a distal end and defining a channel therebetween, at least one opening being defined in a distal portion of the tube; a flexible member having an initial position disposed alongside the tube and being deployable to a subsequent position, the flexible member being configured to be deployable to automatically assume a shape of a greater curvature of a stomach; and a reusable portion having a first tank including a fluid, a second tank for receiving material, and a third tank communicating with atmospheric pressure, the reusable portion having a first valve, a second valve, and a third valve, the first valve and the second valve each having a first position, a second position, and a third position, the channel being delivered with pressurized fluid when the first valve and the second valve are moved to the first position.

52. The medical device according to paragraph 51, wherein the second position of the first valve and the second valve is a closed position.

53. The medical device according to paragraph 51, wherein the third valve has a position in which a vacuum is provided to the channel.

54. The device according to paragraph 51, further comprising a safety feature preventing the third valve from moving to an open position unless the first valve and the second valve are moved to the second position and wherein the second position of the first valve and the second valve is a closed position.

What is claimed is:

1. A method of performing a sleeve gastrectomy in a stomach, comprising:
    inserting a tube into the stomach;
    sliding a distal end portion of a flexible member in a distal direction relative to and along a length of the tube from a contracted position, in which a section of the flexible member is adjacent and external of the tube to a deployed position in which the section of the flexible member bows laterally outward from the tube against a greater curvature of the stomach, wherein the distal end portion of the flexible member is positioned distally of the section of the flexible member when the flexible member is in the deployed position;
    retracting the flexible member; and
    resecting the stomach, thereby forming a sleeve-shaped portion of the stomach.

2. The method according to claim 1, further comprising applying suction to a series of openings in a distal end portion of the tube, thereby placing the tube along a lesser curvature of the stomach and fixing anterior and posterior walls of the stomach.

3. The method according to claim 1, further comprising activating a plurality of illumination devices distributed along a length of the flexible member.

4. The method according to claim 1, wherein in the deployed position, the flexible member pushes the tube toward a lesser curvature of the stomach.

5. A surgical system, comprising:
    a medical device configured for use in resection of a stomach, the medical device including:
        a tube defining a longitudinally-extending channel therethrough, at least one opening being defined in a distal end portion of the tube; and
        a flexible member coupled to the tube and configured to move relative to the tube from a contracted position, in which a section of the flexible member is adjacent and external of the tube to a deployed position in which the section of the flexible member bows laterally outward from the tube against a greater curvature of the stomach, wherein the flexible member has a distal end portion slidably connected to the tube, such that the distal end portion of the flexible member slides distally relative to and along a length of the tube as the section of the flexible member moves toward the deployed position, wherein the distal end portion of the flexible member is positioned distally of the section of the flexible member when the flexible member is in the deployed position; and
    a reusable portion including:
        a first tank having a fluid stored therein;
        a second tank;
        a third tank in communication with atmospheric pressure; and
        first, second, and third valves in communication with the respective first, second, and third tanks, the first valve and the second valve each having at least a first position and a second position, wherein the first tank is configured to deliver the fluid from the first tank to the channel of the tube when the first valve and the second valve are both in the first position.

6. The surgical system according to claim 5, wherein the second position of the first and second valves is a closed position.

7. The surgical system according to claim 5, wherein the first valve is a pressure valve for moving the fluid from the first tank to the channel of the tube.

8. The surgical system according to claim 5, wherein the second valve is a vacuum valve configured to receive the fluid from the channel of the tube.

9. The surgical system according to claim 5, wherein the third valve has a position in which a vacuum is provided to the channel.

10. The surgical system according to claim 5, further comprising a safety feature configured to prevent the third valve from moving to an open position unless the first valve and the second valve are moved to the second position in which the first valve and the second valve are closed.

\* \* \* \* \*